US012534240B2

(12) United States Patent
Arsenault et al.

(10) Patent No.: US 12,534,240 B2
(45) Date of Patent: Jan. 27, 2026

(54) AUTOMATIC PACKAGER FOR MEDICATIONS

(71) Applicant: RXSAFE LLC, Vista, CA (US)

(72) Inventors: Aaron Arsenault, San Diego, CA (US); William K. Holmes, San Diego, CA (US)

(73) Assignee: RXSAFE LLC, Vista, CA (US)

( * ) Notice: Subject to any disclaimer, the term of this patent is extended or adjusted under 35 U.S.C. 154(b) by 121 days.

(21) Appl. No.: 17/916,011

(22) PCT Filed: Apr. 1, 2021

(86) PCT No.: PCT/US2021/025314
§ 371 (c)(1),
(2) Date: Sep. 29, 2022

(87) PCT Pub. No.: WO2021/202835
PCT Pub. Date: Oct. 7, 2021

(65) Prior Publication Data

US 2023/0141858 A1 May 11, 2023

Related U.S. Application Data

(60) Provisional application No. 63/003,798, filed on Apr. 1, 2020.

(51) Int. Cl.

| | |
|---|---|
| ***B65B 5/10*** | (2006.01) |
| ***A61J 1/03*** | (2023.01) |
| ***B65B 57/14*** | (2006.01) |
| ***G16H 20/13*** | (2018.01) |

(52) U.S. Cl.
CPC ............... *B65B 5/103* (2013.01); *A61J 1/035* (2013.01); *B65B 57/14* (2013.01); *G16H 20/13* (2018.01)

(58) Field of Classification Search
CPC ........ A61J 1/035; B65B 39/007; B65B 43/54; B65B 5/103; B65B 5/105; B65B 57/14; G07F 17/0092; G16H 20/13
See application file for complete search history.

(56) References Cited

U.S. PATENT DOCUMENTS

| | | | |
|---|---|---|---|
| 8,406,916 | B2 | 3/2013 | Bentele et al. |
| 10,317,348 | B2 | 6/2019 | Van Den Brink |

(Continued)

FOREIGN PATENT DOCUMENTS

| | | | |
|---|---|---|---|
| EP | 2754614 | A1 | 7/2014 |
| WO | 2017043430 | A1 | 3/2017 |

(Continued)

OTHER PUBLICATIONS

"BlistAssist by RxSafe | Blister Card Filling Automation Solution" By RxSafe, a YouTube video uploaded Nov. 27, 2028; https://www.youtube.com/watch?v=kzJNBhYTD2I (Year: 2018).*

(Continued)

*Primary Examiner* — Himchan Song
(74) *Attorney, Agent, or Firm* — Michael Best & Friedrich LLP

(57) ABSTRACT

An automatic blister card packager (200) is provided. The automatic blister card packager (200) includes a universal feed cassette (205) for individually dispensing medications, a packaging unit (210) in communication with the universal feed cassette (205). The packaging unit (210) is configured to receive a blister card (100). The automatic blister card packager 210 also includes a chute (230) connecting the universal feed cassette (205) to the packaging equipment (210). The chute (230) includes a plurality of tracks (450) and directs the medications dispensed from the universal feed cassette (205) into the blister card (100) received in the packaging equipment (210).

19 Claims, 36 Drawing Sheets

(56) References Cited

U.S. PATENT DOCUMENTS

| | | | | |
|---|---|---|---|---|
| 2009/0044489 | A1 | 2/2009 | Siegel | |
| 2009/0133362 | A1* | 5/2009 | Bentele | B65B 35/18 53/54 |
| 2011/0208352 | A1* | 8/2011 | Knoth | B65B 5/103 700/243 |
| 2013/0212987 | A1 | 8/2013 | Shigeyama et al. | |
| 2013/0318931 | A1* | 12/2013 | Holmes | B65B 9/02 53/562 |
| 2015/0127145 | A1 | 5/2015 | Kim | |
| 2017/0015445 | A1* | 1/2017 | Holmes | G07F 11/165 |
| 2017/0016836 | A1 | 1/2017 | van den Brink | |
| 2018/0265232 | A1* | 9/2018 | Kim | B65B 43/54 |
| 2019/0112080 | A1* | 4/2019 | Holmes | B65B 35/12 |
| 2019/0337647 | A1* | 11/2019 | Yokoyama | G07F 13/025 |
| 2020/0391887 | A1* | 12/2020 | Takada | G07F 11/44 |
| 2023/0141858 | A1* | 5/2023 | Arsenault | B65B 43/54 206/538 |

FOREIGN PATENT DOCUMENTS

| | | | |
|---|---|---|---|
| WO | 2019075462 | A1 | 4/2019 |
| WO | 2019172317 | A1 | 9/2019 |
| WO | 2019195629 | A1 | 10/2019 |
| WO | 2020057807 | A1 | 3/2020 |

OTHER PUBLICATIONS

European Patent Office. Extended European Search Report for Application No. 21781933.3, dated Mar. 28, 2024 (10 pages).

RapidCardRx, Multi-Med, Single Dose, Pre-Pack Adherence Blister Card Packager with Universal Cartridges for any Pharmacy, Product Literature, revised Mar. 30, 2020, (2 Pages).

RapidCardRx, Blister Card Filling Automation, Product information from website: https://rxsafe.com/solutions/rapidcardrx/, accessed Apr. 1, 2020, (9 Pages).

RxSafe, LLC, Announces New Blister Card Pakaging Automation, website: https://www.prweb.com/releases/rxsafe_lie_announces_new_blister_ card_packaging_automation/prweb17017233.htm, Mar. 31, 2020, (3 Pages).

International Search Report with Written Opinion for related Application No. PCT/US2021/025314 dated Aug. 17, 2021, (16 Pages).

BlistAssist by RxSafe, Blister Card Filling Automation Solution (RxSafe), Nov. 27, 2018, retrieved from URL: https://www.youtube.com/watch?v=kzJNBhYTD2I>, 2 screenshots.

* cited by examiner

AUTOMATIC PACKAGER FOR MEDICATIONS

CROSS-REFERENCE TO RELATED APPLICATIONS

This application claims priority to U.S. Provisional Patent Application No. 63/003,798, filed Apr. 1, 2020, the entire contents of which are incorporated by reference herein.

FIELD OF THE INVENTION

The present invention relates to an automatic packager for medications. More particularly, the present invention relates to an automatic packager for pharmaceutical blister card packages.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Pharmacies use several types of packaging to provide pharmaceutical products or medications to consumers. The types of packaging may include strip packages, blister cards, pill vials, and the like. Pill vials and strip packages are most appropriate for individual customers of retail pharmacies. However, institutional customers, for example, nursing homes, palliative or hospice facilities, hospitals, and the like use blister cards extensively.

Figure 1:
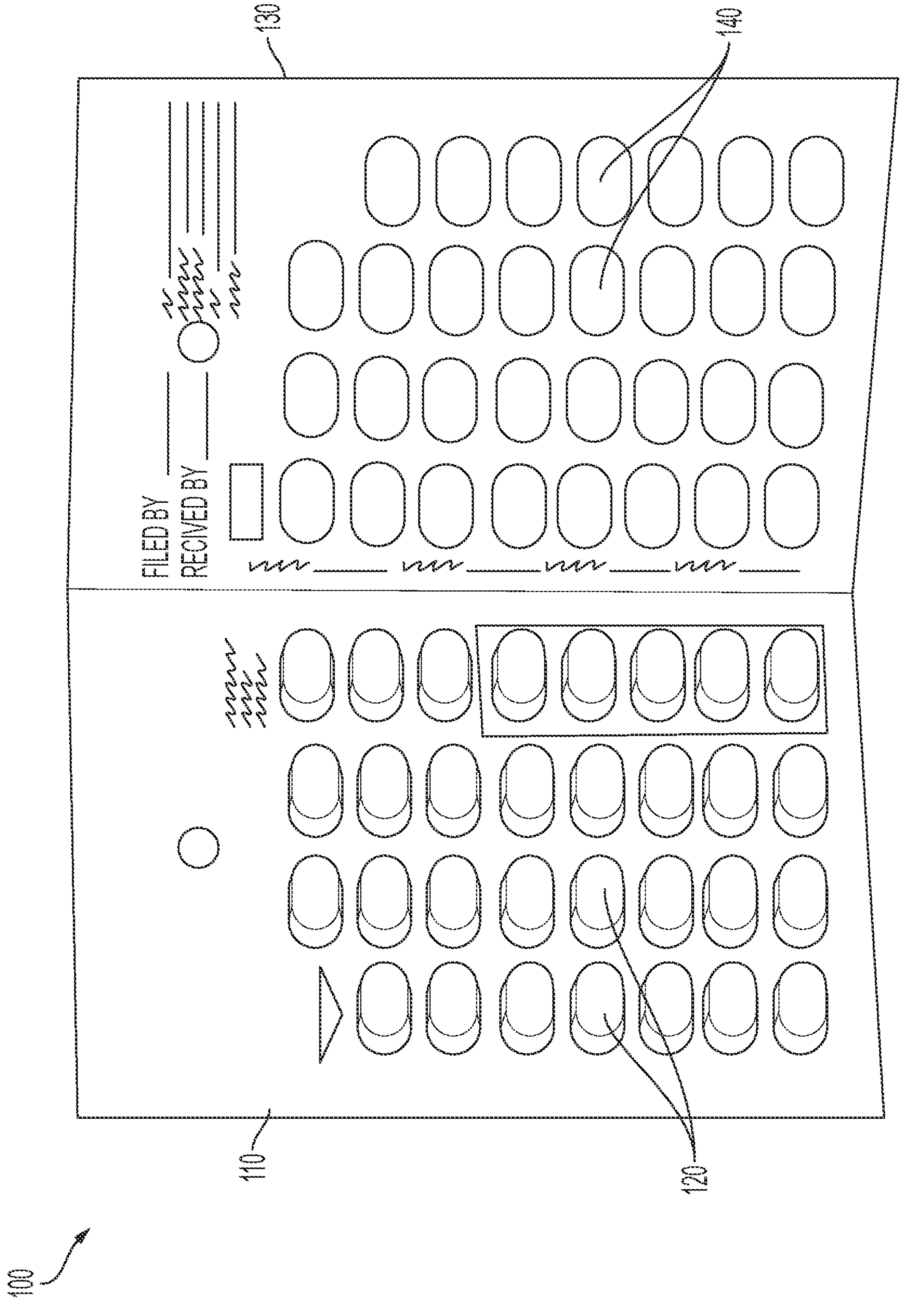
FIG. 1 illustrates a blister card in accordance with some embodiments.

FIG. 1 illustrates an example of a blister card 100. The blister card 100 includes a blister sheet 110 including thirty to thirty-two blister compartments 120. Each blister compartment 120 may receive a single unit of medication or may receive more than a single unit of medication. When the blister compartments 120 are filled, a label sheet 130 is attached to the back of the blister sheet 110 to seal the blister compartments 120. The label sheet 130 includes information regarding the blister card 100 including, for example, a facility name, a patient name, a medication name, a medication dose, and the like. The label sheet 130 includes seal portions 140 aligned with each blister compartment 120 such that a user may tear the seal portions 140 to retrieve the packaged medication.

In the example illustrated in FIG. 1, the blister card 100 is, for example, a standard 6"×9" card. In other embodiments, the blister card 100 may be other sizes. The blister card 100 may be used for filling different amounts of pills for different periods of time. For example, the blister card 10 may be used for one week of pills (e.g., 7 pills), for up to four weeks or a month of pills (e.g., 28-31 pills), or more. In some embodiments, the blister card 100 is a "pre-pack" having only one medication in some or all the blister compartments 120. In other embodiments, the blister card 100 may include more than one pill in the same blister compartment 120 or distributed among the different blister compartments 120. In the example illustrated, the label sheet 130 is shown attached to the blister sheet 110; however, the label sheet 130 may be separately provided from the blister sheet 110. The label sheet 130, whether provided with the blister sheet 110 or separate from the blister sheet 110, may be cold sealed or hot sealed with the blister sheet 110 after filling. In some embodiments, a bar code may printed on the label sheet 130 to provide identification information. The bar code may be scanned to retrieve information regarding the blister card 100 as provided above. The bar code may be pre-printed before filling or may be printed after filling to uniquely identify the blister card 100. This bar code may be later used by a filling machine to identify that a correct blister card 100 is currently being filled.

Automatic strip packages are now used in retail pharmacies to quickly and accurately package medications into strip packages. Automatic strip packagers have allowed pharmacies to fulfill more customer orders in a relatively short time and with more accuracy than hand-filling vials. Accordingly, more and more pharmacies are now using automatic strip packagers to serve individual customers. On the other hand, a majority of blister cards are still filled by hand. Hand filling is performed by placing the blister sheet 110 on a table or on a hand-filling machine. A technician or pharmacist then hand fills each blister compartment 120 before sealing the blister card 100. Hand-filling machines help verify accurate filling of the blister card 100 but do not themselves speed up the blister card 100 filling process.

Current blister card packagers available in the market are expensive, inefficient, and are generally not a good replacement for filling blister cards 100 by hand. Existing machines generally take up a large area and do not provide a cost benefit over hand filling the blister cards 100.

Figure 2:
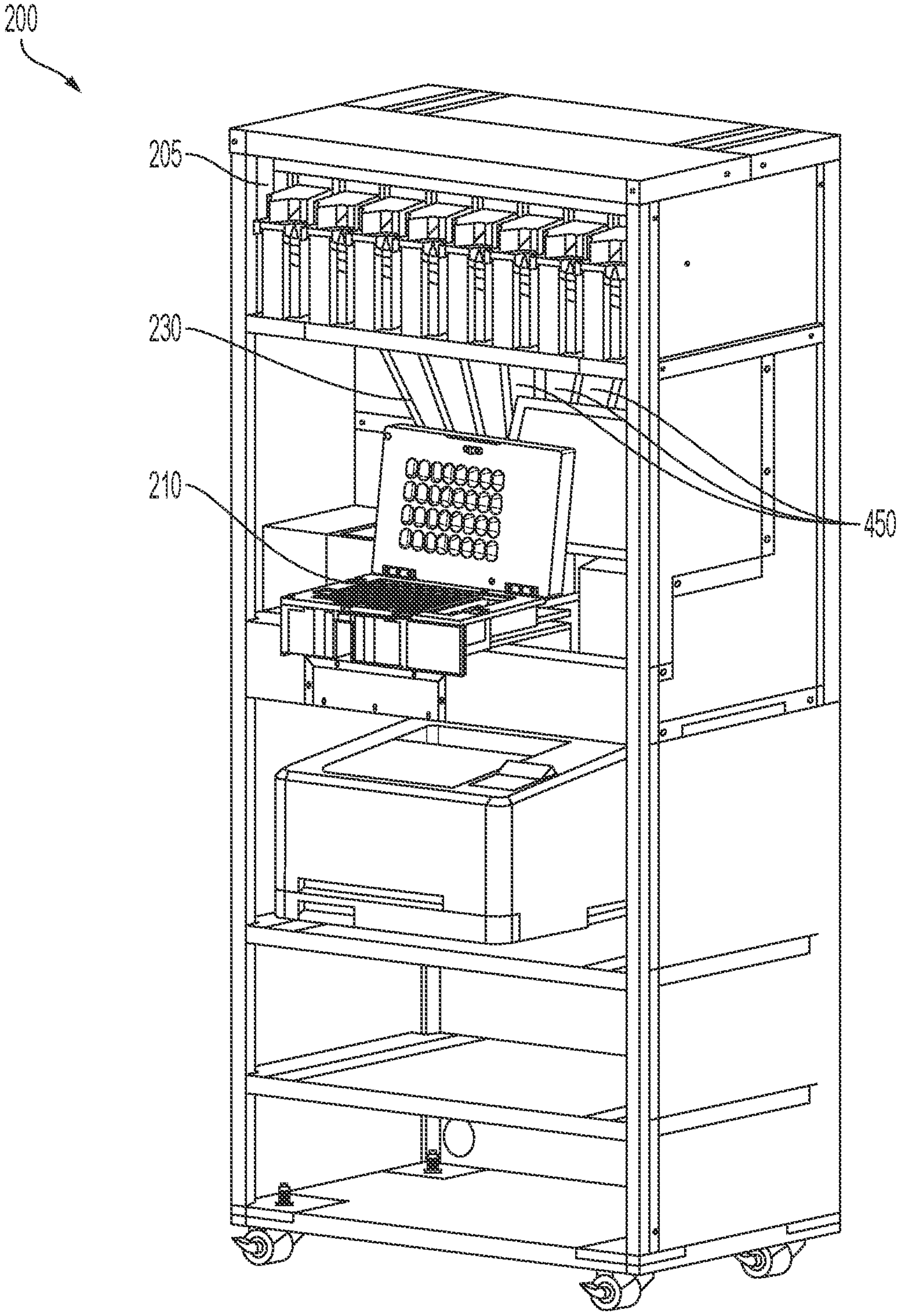
FIG. 2 is a perspective view of an automatic blister card packager in accordance with some embodiments.

FIG. 2 illustrates an example of an automatic blister card packager 200 that efficiently packages blister cards 100 in a quick and accurate manner. In the example illustrated, the automatic blister card packager 200 includes a universal feed cassette 205 and a packaging unit 210. The universal feed cassette 205 receives medications from the bulk canisters and individually dispenses pills to the packaging unit 210. Each universal feed cassette 205 may dispense eight separate pills at the same time. In the example illustrated in FIG. 1, the automatic blister card packager 200 includes one universal feed cassette 205; however, the automatic blister card packager 200 may include more than one universal feed cassette 205 to dispense more than eight pills at the same time.

Figure 3:
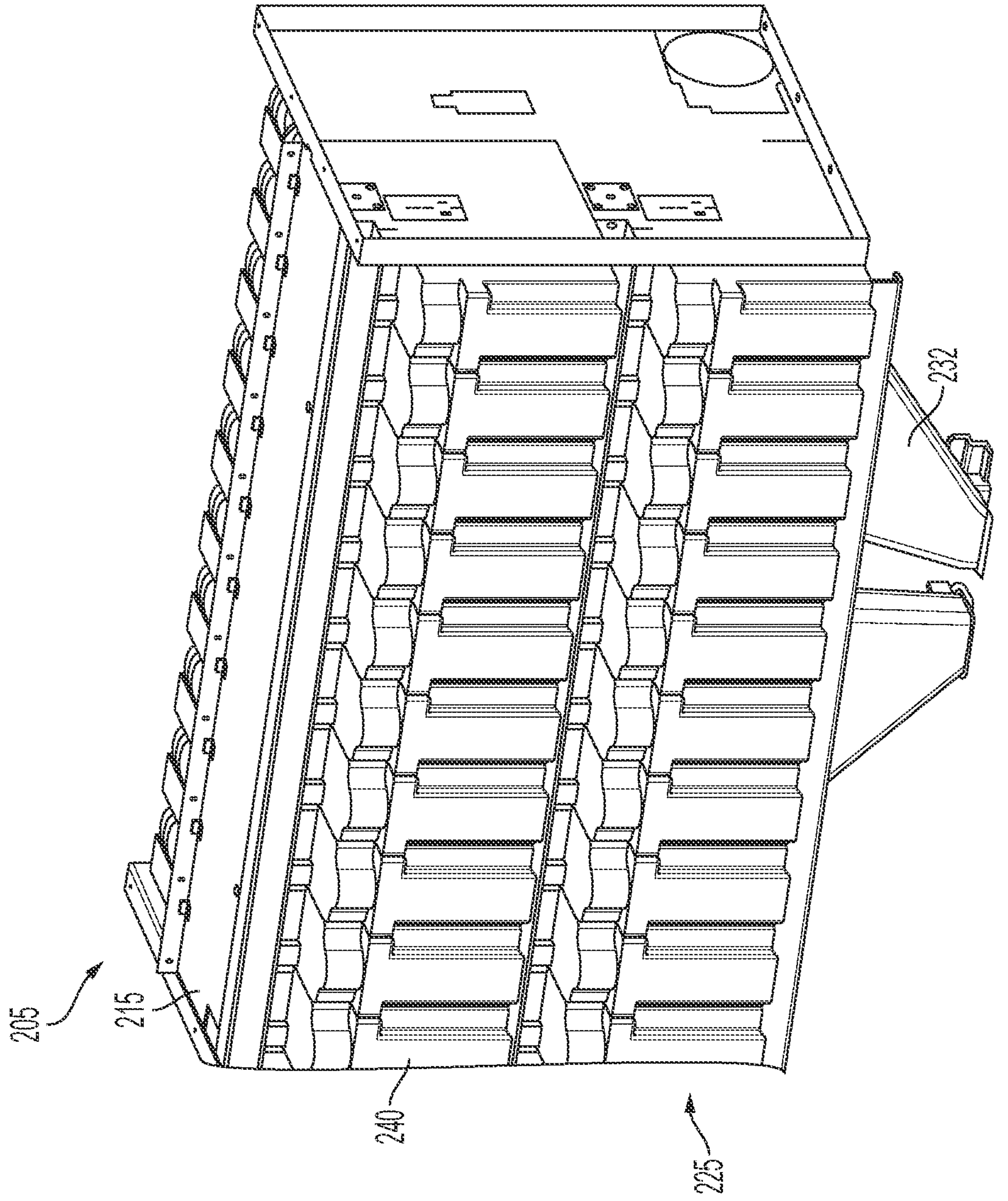
FIG. 3 is a front perspective view of a universal feed cassette of the automatic blister card packager of FIG. 2 in accordance with some embodiments.
Figure 4:
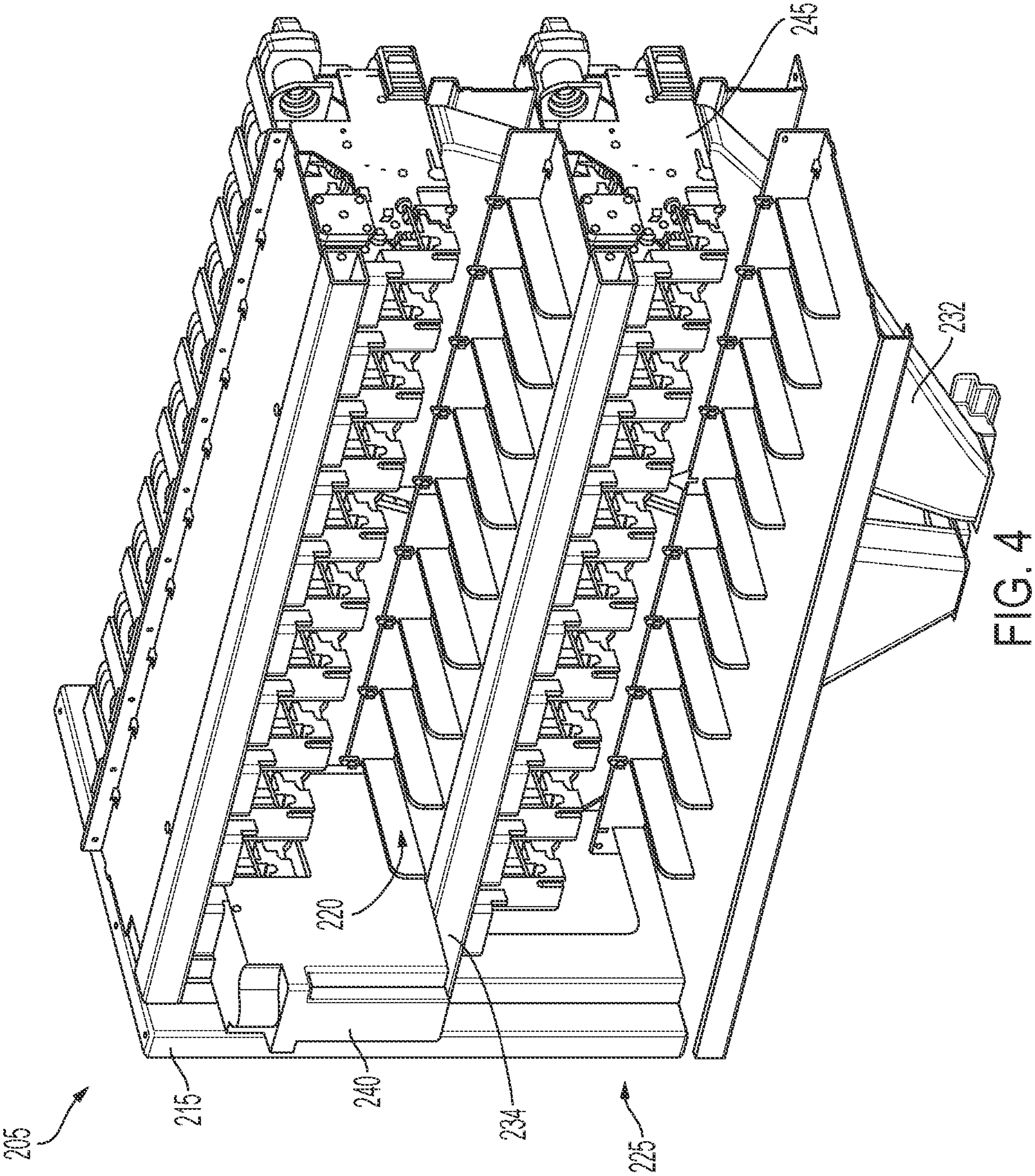
FIG. 4 is a front perspective view of the universal feed cassette of FIG. 3 with a part of a housing removed in accordance with some embodiments.
Figure 5:
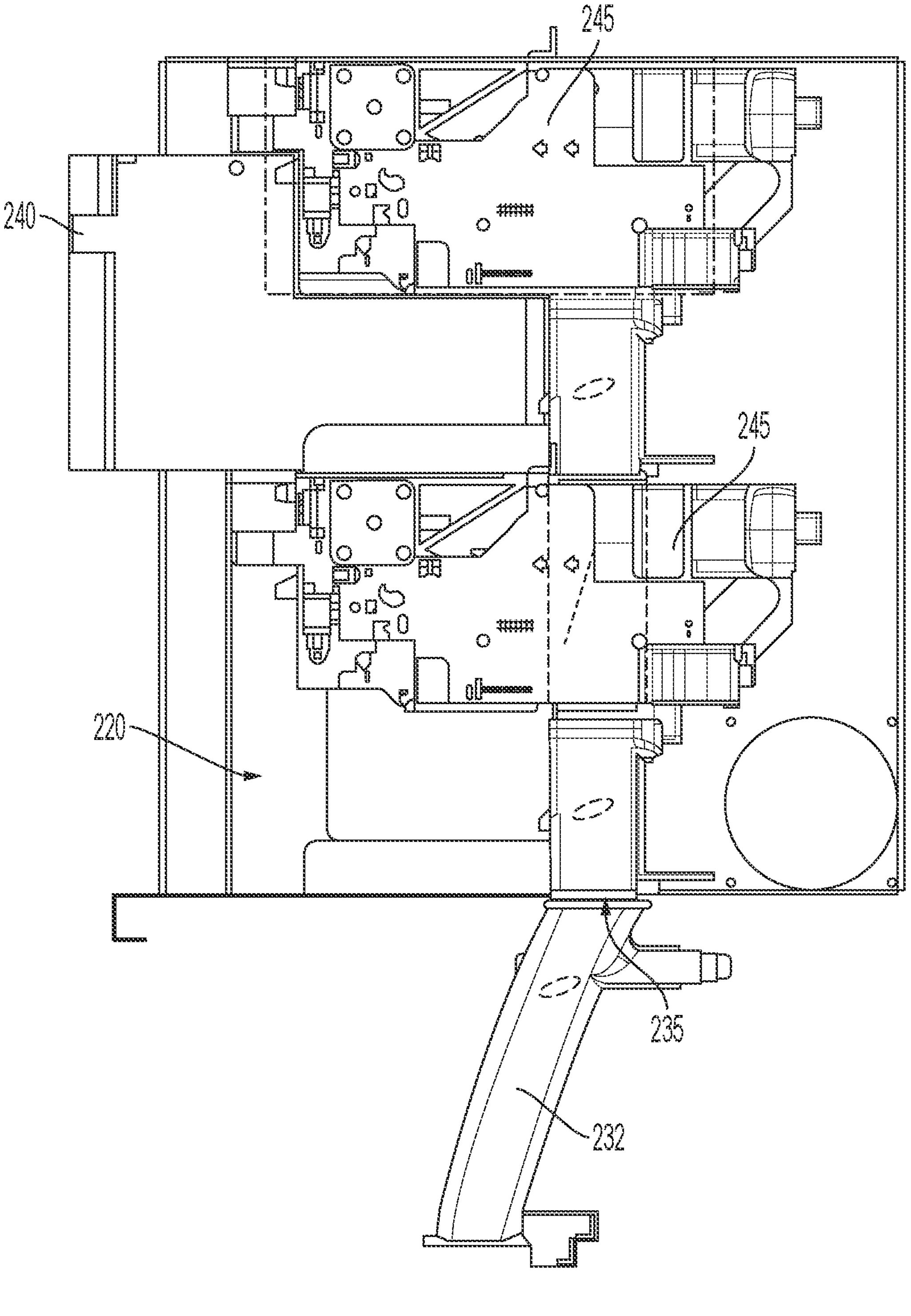
FIG. 5 is a plan view of the universal feed cassette of FIG. 3 in accordance with some embodiments.
Figure 6:
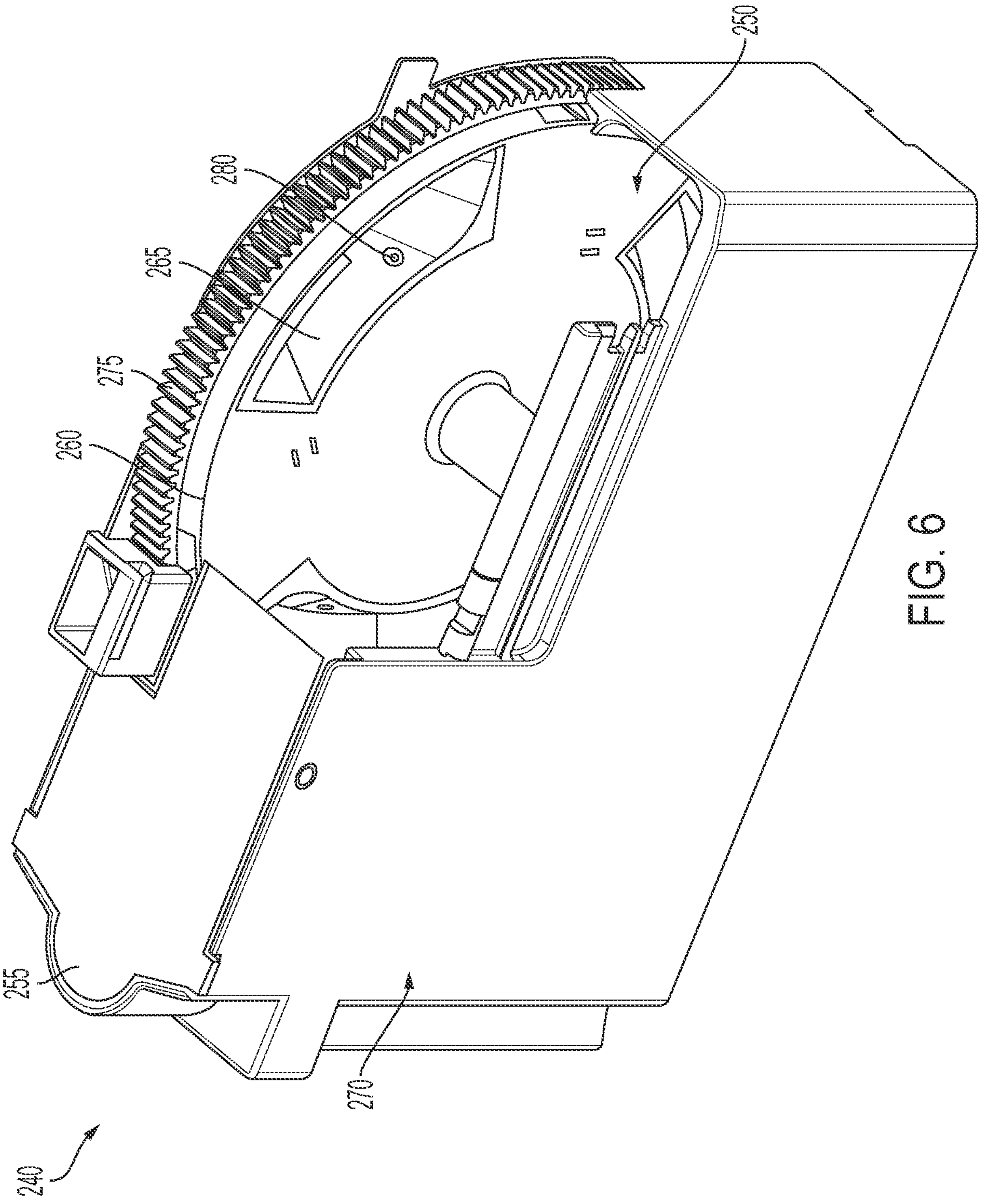
FIG. 6 is a perspective view of a cartridge of the universal feed cassette of FIG. 3 in accordance with some embodiments.

Referring to FIGS. 3-5, the universal feed cassette 205 includes a housing 215 having a plurality of cartridge slots 220 within the housing 215. An opening 225 is provided on a front side (e.g., a first side) of the housing 215 and a cassette cover covers a back side (e.g., a second side) of the housing 215. Dispensing openings 235 are provided on the bottom of the housing 215. The dispensing openings 235 are in communication with a chute 230 of the automatic blister card packager 200.

In the example illustrated in FIGS. 3-5, the universal feed cassette 205 includes up to sixteen cartridge slots 220. In some embodiments, the cartridge slots 220 are arranged in a duplex-formation such that a second row of cartridge slots 220 are provided above a first row of cartridge slots 220 within the housing 215 to facilitate faster filling of blister cards 100. FIG. 5 illustrates a side-profile view of the duplex-formation of the cartridge slots 220. A separating platform 234 is provided between the first row and the second row of cartridge slots 220. In some embodiments, the universal feed cassette 205 may only include a single row of cartridge slots 220, or may include more than two rows of cartridge slots 220. The cartridge slots 220 receive cartridges 240 through the opening 225. A plurality of cartridge mechanisms 245, one for each cartridge slot 220 is fixed to the top of the housing 215—for the second row of cartridge slots 220—and the separating platform 234—for the first row of cartridge slots 220. When received in the cartridge slots 220, the cartridges 240 are connected to the cartridge mechanism 245. The cartridge mechanism 245 individually dispenses medications 180 from the cartridge 240 as described in detail below. The dispensing openings 235 transfer the medications 180 from the cartridges 240 to the packaging unit 210 for packaging. The cassette cover can be removed to access the cartridge mechanisms 245 from the back side of the housing 215. The cartridge mechanisms 245 are removably fixed to the housing 215 such that a technician can remove a cartridge mechanism 245 for servicing.

Referring to FIGS. 6-9, the cartridge 240 includes a reservoir 250, a reservoir cover 255, a wheel 260, and scooping members 265. The reservoir 250 stores the medications 180 during the dispensing process. The wheel 260 is provided on one side of the cartridge 240 and extends into the bottom portion of the reservoir 250. The bottom portion of the reservoir 250 has a curved shape starting from the side opposite that of the wheel 260, the front side, and the back side and ending at the center of the bottom portion of the wheel 260 (see FIG. 9). The curved shape of the reservoir 250 directs the medications 180 within the reservoir 250 towards the bottom of the wheel 260 and particularly into the scooping members 265 of the wheel 260.

The reservoir cover 255 covers a portion (e.g., a spout portion 270) of the reservoir 250. The reservoir cover 255 is pivotably attached to the spout portion 270 to pivot between an open position and a closed position. When a pharmacist is emptying the contents of the cartridge 240, the reservoir cover 255 pivots to the open position to allow the medications 180 to flow out of the reservoir 250 into the bulk containers. During the dispensing process, the cartridge mechanism 245 includes a stopper 246 to inhibit the reservoir cover 255 from opening. As such, the medications 180 within the reservoir 250 are not accessible outside the machine during the dispending process.

Teeth 275 are provided on the outer circumferential surface of the wheel 260. During the dispensing process, the teeth 275 interlock with teeth of a shaft driven by a motor assembly of the cartridge mechanism 245. The wheel 260 is provided with three scooping members 265 to scoop individual medications 180 from the reservoir 250. The scooping members 265 include an inward projection 266 extending into the wheel 260. The curved surface of the reservoir 250 guides the medications 180 into the inward projections of the scooping members 265. The scooping members 265 include a stopper 268 along a circumferential end of the inward projections that hold the medications 180 when the wheel 260 is being rotated. Scooping members 265 may be made in different sizes to accommodate the different sizes of medications 180. The scooping members 265 can be swapped to configure the cartridges 240 to dispense medications 180 of different sizes. The scooping members 265 may also be removed for cleaning. In some embodiments, rather than being separate from the wheel 260, the scooping members 265 may be formed integrally with the wheel 260. In these embodiments, the wheels 260 or cartridges 240 may be swapped to dispense medications 180 of different sizes.

Figure 11:
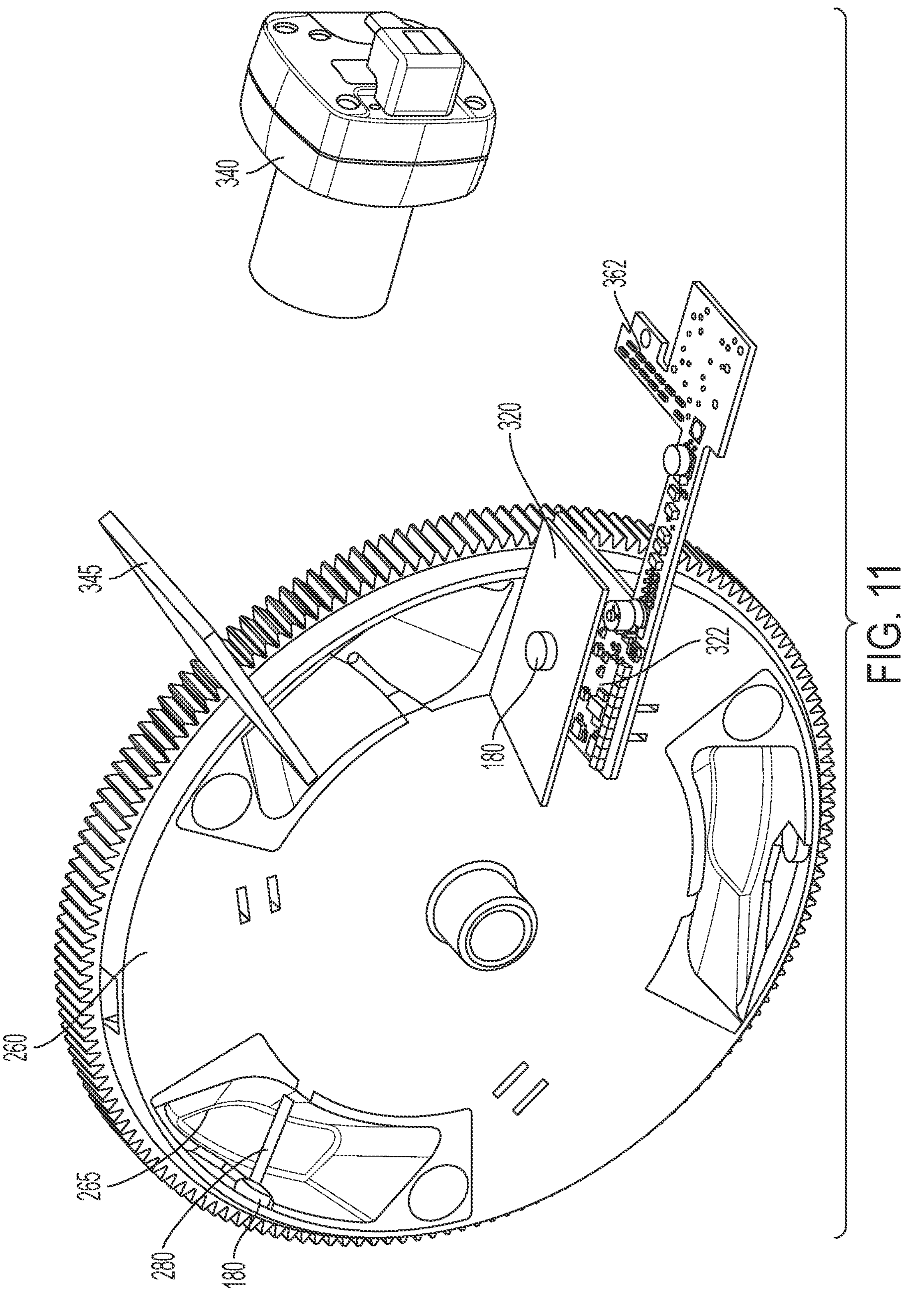
FIG. 11 is a perspective view of a wheel of the cartridge of FIG. 6 and a camera system and a shuttle system of the cartridge mechanism of FIG. 10 in accordance with some embodiments.
Figure 12:
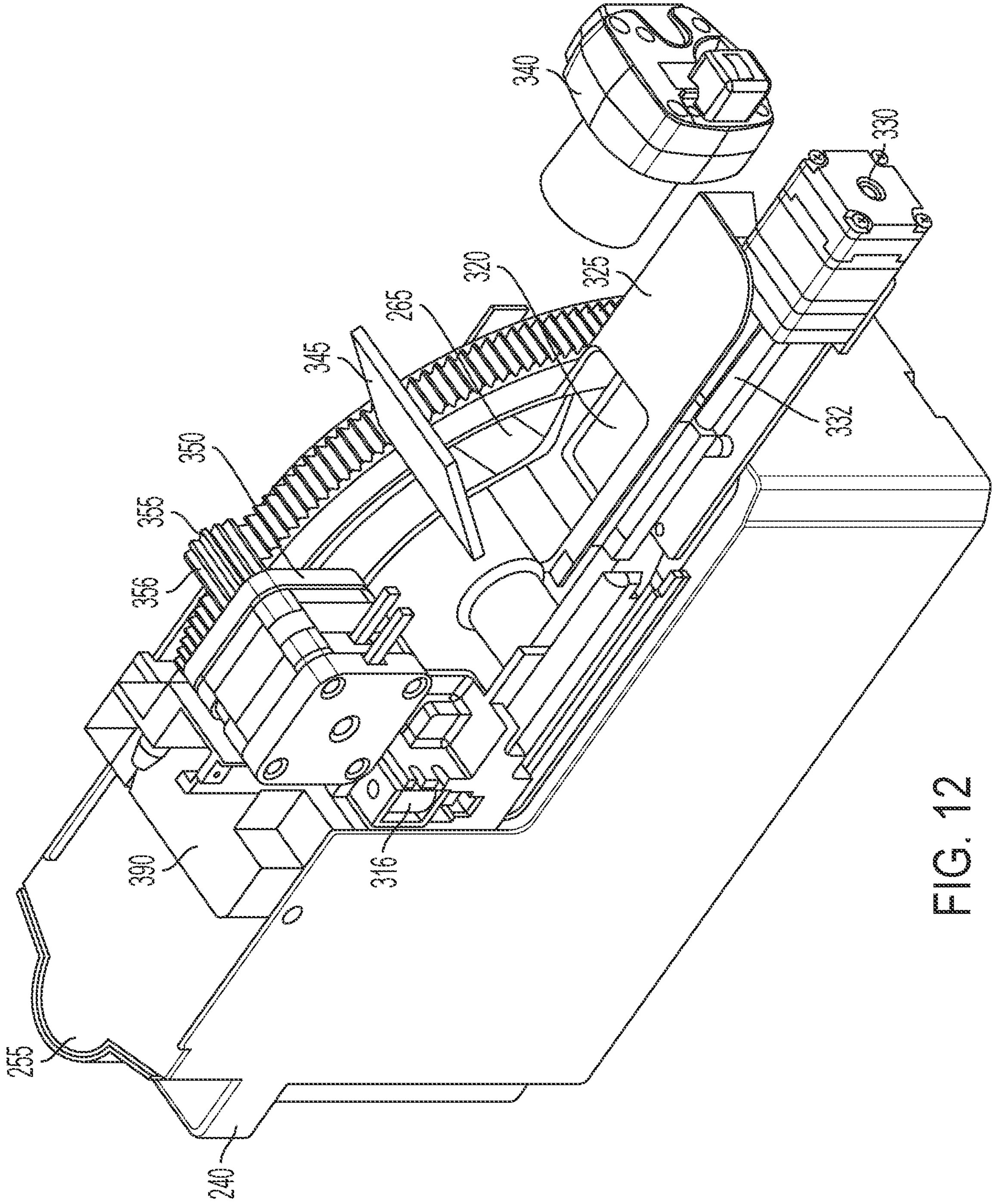
FIG. 12 is a perspective view of the cartridge of FIG. 6 and the cartridge mechanism of FIG. 10 in accordance with some embodiments.
Figure 13:
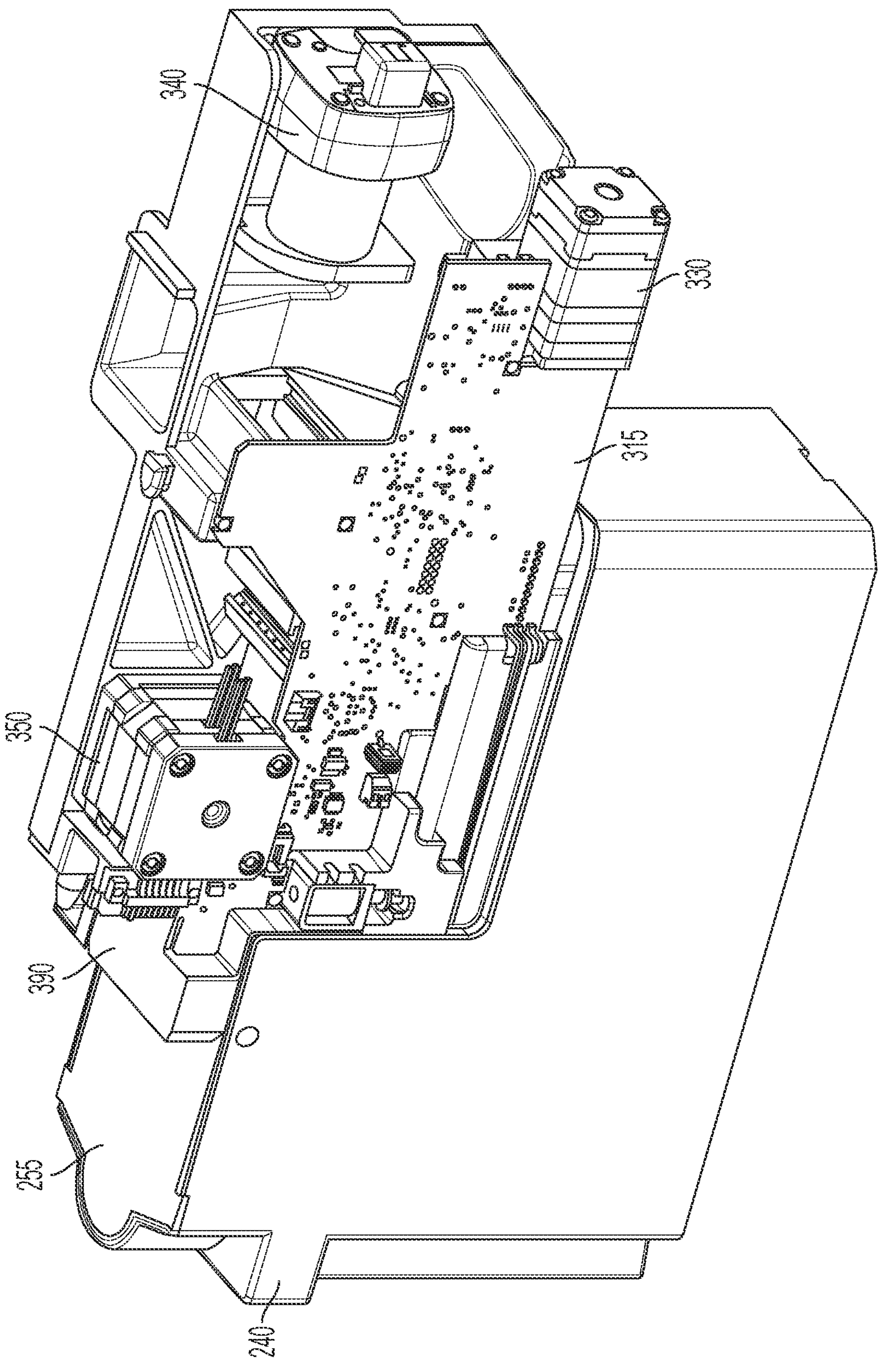
FIG. 13 is a perspective view of the cartridge of FIG. 6 and the cartridge mechanism of FIG. 10 in accordance with some embodiments.

The wheel 260 includes holding pins 280 (see FIG. 11) that extend and retract from the inside of the wheel 260 during rotation of the wheel 260. The scooping members 265 include an opening to receive the holding pins 280. The holding pins 280 along with the stopper and the circumferential surface of the inward projection 266 are used to hold a medication 180 when the wheel 260 is being rotated. During rotation of the wheel 260, when the inward projections 266 of the scooping members 265 encounter the reservoir 250, the medications 180 in the reservoir 250 move inward into the scooping members 265 due to the curved shape of the reservoir 250. The holding pins 280 are retracted when the scooping members 265 are moving along the reservoir 250 at a bottom portion of the wheel 260. As the scooping members 265 move out of the reservoir 250, the holding pins 280 are advanced towards the circumferential end of the scooping members 265 to engage a medication 180. The medications 180 are held between the circumferential end of the scooping member 265, the holding pin 280, and the stopper 268. The scooping member 265 and the holding pin 280 can be used for any type of medication 180. Typically, only a single medication 180 is pinched between the holding pin 280 and the scooping member 265, while the other medications 180 fall back into the reservoir 250 during the rotation of the wheel 260. As the scooping member 265 passes the top portion of the wheel 260, the holding pin 280 is once again retracted to release the medication 180 into the cartridge mechanism 245. The wheel 260 and the scooping member 265 may together be referred to as a singulating mechanism.

Figure 7:
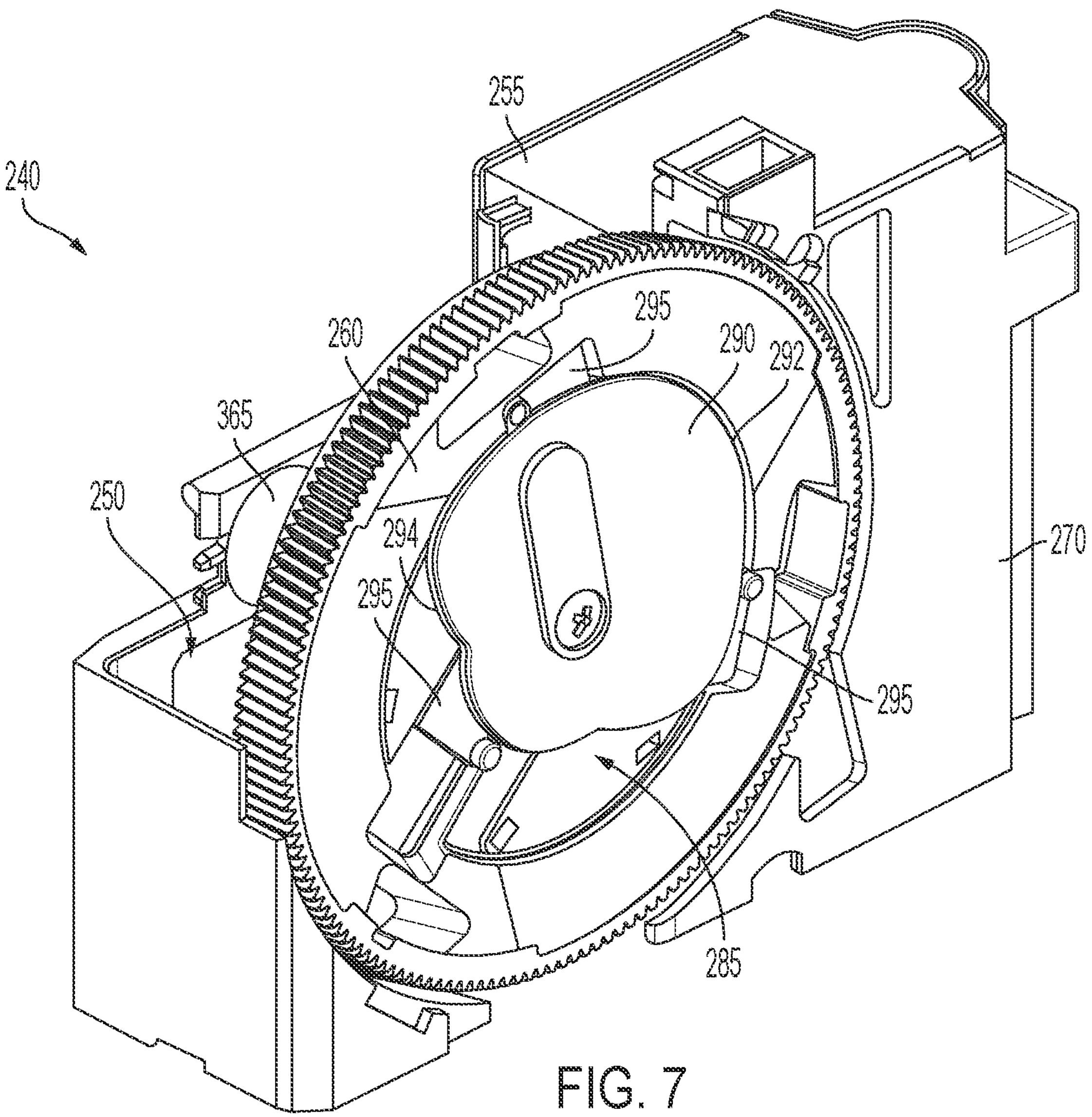
FIG. 7 is a back perspective view of the cartridge of FIG. 6 in accordance with some embodiments.
Figure 8:
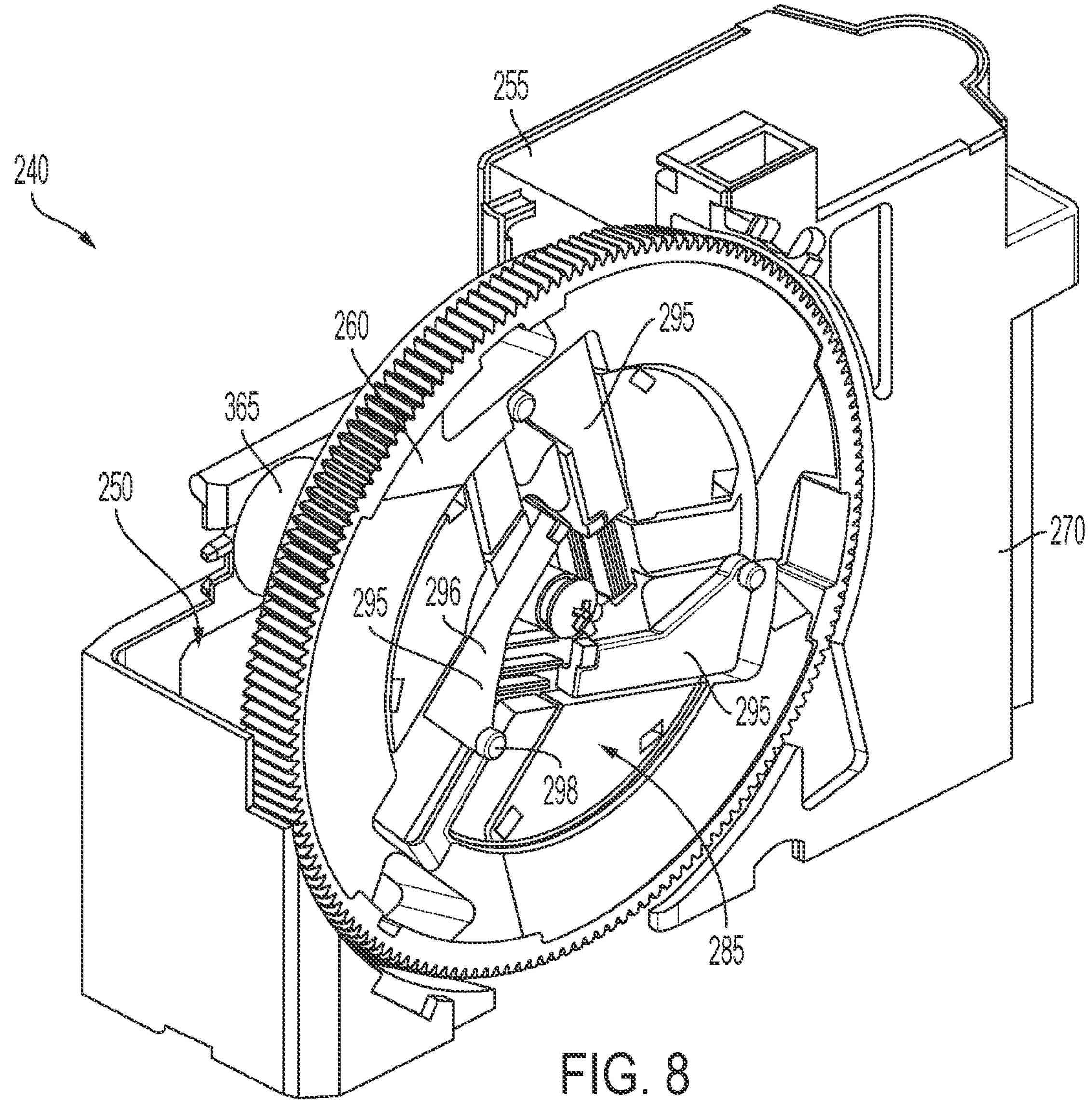
FIG. 8 is a back perspective view of the cartridge of FIG. 6 in accordance with some embodiments.

FIGS. 7 and 8 illustrate a cam and follower mechanism 285 that is used to advance and retract the holding pins 280. The cam and follower mechanism 285 is provided in the wheel 260. The cam and follower mechanism 285 includes a cam 290 and a plurality of followers 295. In the example illustrated, the cartridge 240 includes three followers 295, one for each of the holding pins 280. The holding pins 280 are attached to the followers 295 to move with the followers 295. The cam 290 is fixed to the cartridge 240 and remains stationary even when the wheel 260 is rotated. The cam 290 includes an arc portion 292 and a cut-off portion 294. The arc portion 292 extends further from the center of the cam 290 than the cut-off portion 294. The follower 295 includes a flat portion 296 that is coupled to a holding pin 280 and an outward projection 298 extending from the flat portion 296 to engage the circumferential surface of the cam 290. A spring mechanism is connected to a radially inward end of the followers 295 to provide an inward biasing force to the followers 295. The holding pin 280 is advanced when the corresponding follower 295 engages the arc portion 292 of the cam 290 and is retracted when the corresponding follower 295 engages the cut-off portion 294 of the cam 290. The follower 295 is retracted due to the biasing force of the spring mechanism when the follower 295 engages the cut-off portion 294 of the cam 290.

Referring to FIGS. 10-14, the cartridge mechanism 245 includes a shuttle system 300 (for example, a verification system), a camera system 305, a motor assembly 310, a printed circuit board 315, and a lockout mechanism 316. The shuttle system 300, shown in FIG. 12, includes a platform 320, a shuttle 325, and a shuttle drive 330. The platform 320 may be made from a clear or translucent plastic material. An LED lighting system 322, as described above, may be provided over and/or under the platform 320 to illuminate the contents on the platform 320 when the camera system 305 is capturing an image of the contents. The LED lighting system 322 may emit visible or infrared light to illuminate the platform 320.

Typically, a single LED device may be used below the platform 320 to illuminate the translucent platform 320. However, the single LED device may not provide uniform lighting through all of the surface area of the platform 320. Particularly, each LED device includes a light signature such that the center of the platform 320 is brighter than the edges of the platform. This irregularity in brightness may result in misidentifying medications 180 during the image recognition process. In order to provide uniform brightness across the surface are of the platform, several LED devices may be placed around the bottom surface of the platform. In some embodiments, the light signature of the LED device is detected and a backing (not shown) may be applied to the platform to correct the light signature of the LED device. The backing, when applied to the platforms 320, distributes the light from the LED device of the LED lighting system 322 such that every portion of the platform 320 is illuminated with similar brightness.

The shuttle 325 may be moved laterally between the platform 320, over the reservoir 250, and over a conduit 335. The shuttle 325 transfers the medications from the platform 320 either to the reservoir 250 or to the conduit 335. The shuttle 325 is driven by the shuttle drive 330. The shuttle drive 330 may be a motor assembly, an actuator, or the like that moves the shuttle 325 between the platform 320, over the reservoir 250, and over the conduit 335. In the example illustrated, the shuttle drive 330 includes a rotating screw 332 that moves the shuttle 325 laterally between the platform 320, the reservoir 250, and the conduit 335.

The camera system 305 includes a camera 340 and a mirror 345. The camera 340 is positioned at the back of the cartridge mechanism 245. The camera 340 may be a still camera or a video camera that captures an image of the contents of the platform. The mirror 345 is placed directly above the platform 320 and is tilted at a 45-degree angle such that the camera 340 positioned at the back of the cartridge mechanism 245 can capture an image of the platform 320.

The motor assembly 310 includes a motor 350 that drives a shaft 355 positioned in the middle of the cartridge mechanism 245. The shaft 355 includes teeth 356 that interlock with the teeth 275 of the wheel 260 (see FIG. 12). When the motor 350 is driven, the shaft 355 rotates the wheel 260 to individually dispense the medications 180.

The PCB 315 includes the electrical components of the cartridge mechanism 245. The PCB 315 is positioned on the side opposite that of the wheel 260. In some embodiments, the PCB 315 includes an antenna 360 (see FIG. 10) that detects an RFID tag 365 (see FIG. 7-9) placed on the cartridge 240. The RFID tag 365 may store information of the cartridge 240. The information stored on the RFID tag 365 may include, for example, identification information of the cartridge 240, medication restrictions (e.g., dedicated to allergenic medication or non-allergenic medication) of the cartridge 240, and the like.

The lockout mechanism 316 is, for example, a lockout solenoid that prevents a cartridge 240 from being loaded onto the cartridge mechanism 245 when the lockout mechanism 316 is activated. During a dispensing process, not all cartridge mechanisms 245 are used to fill a prescription. In these situations, the lockout mechanism 316 is used to prevent cartridges 240 from being placed on inactive cartridge mechanism 245. In addition, the lockout mechanism 316 may be used to prevent an incompatible or wrong cartridge 240 from being loaded to the cartridge mechanism 245. For example, the cartridge mechanism 245 may read the RFID tag 365 to determine whether the correct and compatible cartridge 240 is being loaded to the cartridge mechanism 245. The cartridge mechanism 245 may only deactivate the lockout mechanism 316 when the correct cartridge 240 is being loaded to the cartridge mechanism 245. The lockout mechanism 316 may also be used to prevent the cartridge 240 from being removed from the cartridge mechanism 245. Particularly, the lockout mechanism 316 locks the cartridge 240 in place when loaded on to the cartridge mechanism 245. During the dispensing process, the lockout mechanism 316 is activated to prevent removal of the cartridge 240. The lockout mechanism 316 may be deactivated when the dispensing process is complete and the cartridge 240 can be removed from the cartridge mechanism 245.

Figure 14:
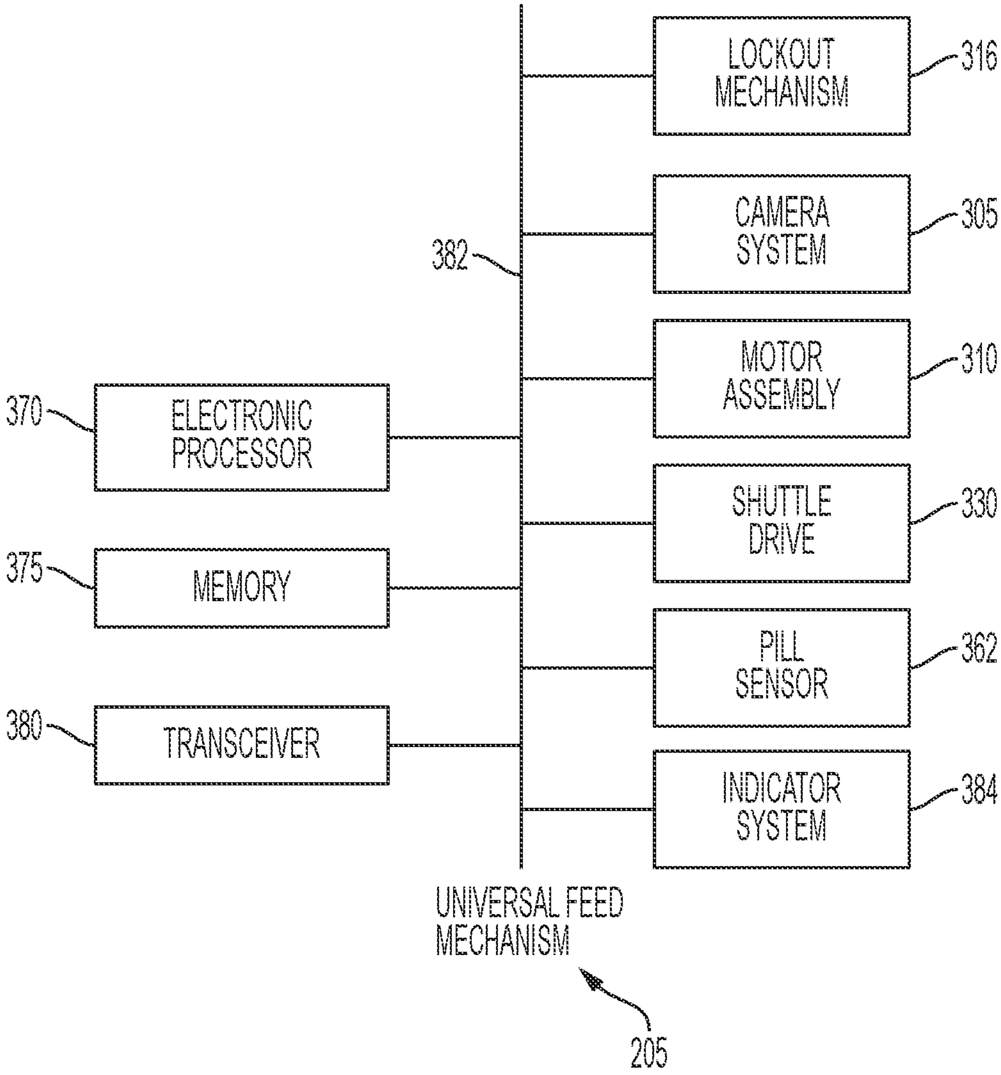
FIG. 14 is a block diagram of the cartridge mechanism of FIG. 10 in accordance with some embodiments.

FIG. 14 is a block diagram of one embodiment of the universal feed cassette 205. In the example illustrated, the universal feed cassette 205 includes an electronic processor 370, a memory 375, a transceiver 380, the camera systems 305, the motor assemblies 310, the lockout mechanisms 316, the shuttle drives 330, the antennas 360, the pill sensors 362, and indicator systems 384. The electronic processor 370, the memory 375, the transceiver 380, the camera system 305, the motor assembly 310, the lockout mechanism 316, the shuttle drive 330, and the pill sensor 362 communicate over one or more control and/or data buses (for example, a communication bus 382). FIG. 14 illustrates only one example embodiment of the cartridge mechanism 245. The cartridge mechanism 245 may include more or fewer components and may perform functions other than those explicitly described herein.

In some embodiments, the electronic processor 370 is implemented as a microprocessor with separate memory, such as the memory 375. In other embodiments, the electronic processor 370 may be implemented as a microcontroller (with memory 375 on the same chip). In other embodiments, the electronic processor 370 may be implemented using multiple processors. In addition, the electronic processor 370 may be implemented partially or entirely as, for example, a field-programmable gate array (FPGA), an applications specific integrated circuit (ASIC), and the like, and the memory 375 may not be needed or be modified accordingly. In the example illustrated, the memory 375 includes non-transitory, computer-readable memory that stores instructions that are received and executed by the electronic processor 370 to carry out the functionality of the cartridge 240 described herein. The memory 375 may include, for example, a program storage area and a data storage area. The program storage area and the data storage area may include combinations of different types of memory, such as read-only memory and random-access memory. FIG. 14 illustrates the universal feed cassette 205 as including a single electronic processor 370 and a single memory 375. However, it should be noted that the universal feed cassette 205 may include separate electronic processor 370 and separate memories with one each for each of the cartridge mechanisms 245. Accordingly, in some embodiments, a single processor performs the functions of the universal feed cassette 205 including all of the cartridge mechanisms 245 of the universal feed cassette 205. In other embodiments, the functions of the universal feed cassette 205 and the cartridge mechanisms 245 may be divided between several processors.

The transceiver 380 enables wired or wireless communication between the electronic processor 370 and a control system of the automatic blister card packager 200 and/or a control system of the packaging unit 210. In some embodiments, the transceiver 380 may include separate transmitting and receiving components, for example, a transmitter and a receiver.

The other components of the universal feed cassette 205 are described singularly with respect to a single cartridge mechanism 245. However, it should be noted that the descriptions and functionality are equally applicable for each cartridge mechanism 245 of the universal feed cassette 205. The camera system 305 receives control signals from the electronic processor 370. Based on the control signals received from the electronic processor 370, the camera system 305 controls the camera 340 and the lighting system that illuminates the platform 320. The motor assembly 310 may send position sensor signals to the electronic processor 370 and receive control signals to operate a motor of the motor assembly 310 based on the position sensor signals. As described above, the shuttle drive 330 may be a motor assembly or an actuator. The shuttle drive 330 may also include a position sensor to determine the position of the shuttle 325. The shuttle drive 330 may send the position sensor signals to the electronic processor 370, which sends control signals to the shuttle drive 330 to move the shuttle 325 based on the position sensor signals. In some embodiments, the shuttle system 300 may also include a shuttle home sensor, which indicates whether the shuttle 325 is at a home position. Signals from the shuttle home sensor are provided to the electronic processor 370 to control the movement of the shuttle 325.

The pill sensor 362 communicates with the electronic processor 370 to provide an indication of whether or not a pill is dispensed through the conduit 335. The electronic processor 370 also controls the indicator system 364 to provide an indication of the status of each cartridge 240. The indicator system 384 may include one or more LEDs provided behind a translucent plastic material. The electronic processor 370 may use the indicator system 384 to provide indications, for example, whether a cartridge 240 is correctly placed in the cartridge slot 220. The electronic processor 370 may activate, for example, a blue LED to indicate that a next cartridge 240 should be placed in the corresponding cartridge slot 220 (that is, the cartridge slot 220 corresponding to the cartridge mechanism 245 with the blue LED activated). The electronic processor 370 may activate, for example, a green LED to indicate that the cartridge 240 was correctly placed in the cartridge slot 220. The electronic processor 370 may activate, for example, a red LED to indicate that the cartridge 240 was not correctly placed in the cartridge slot 220. Additionally, the electronic processor 370 may use the indicator system 384 to provide indications on where to place a cartridge 240 and when to remove a cartridge 240. For example, the electronic processor 370 may activate a blue LED to indicate that a pharmacist can place a cartridge 240 in the cartridge slot 220 corresponding to the activated LED. The electronic processor 370 may activate a blue LED again to indicate that the dispensing process is complete and the cartridge 240 can be removed from the cartridge slot 220.

Figure 9:
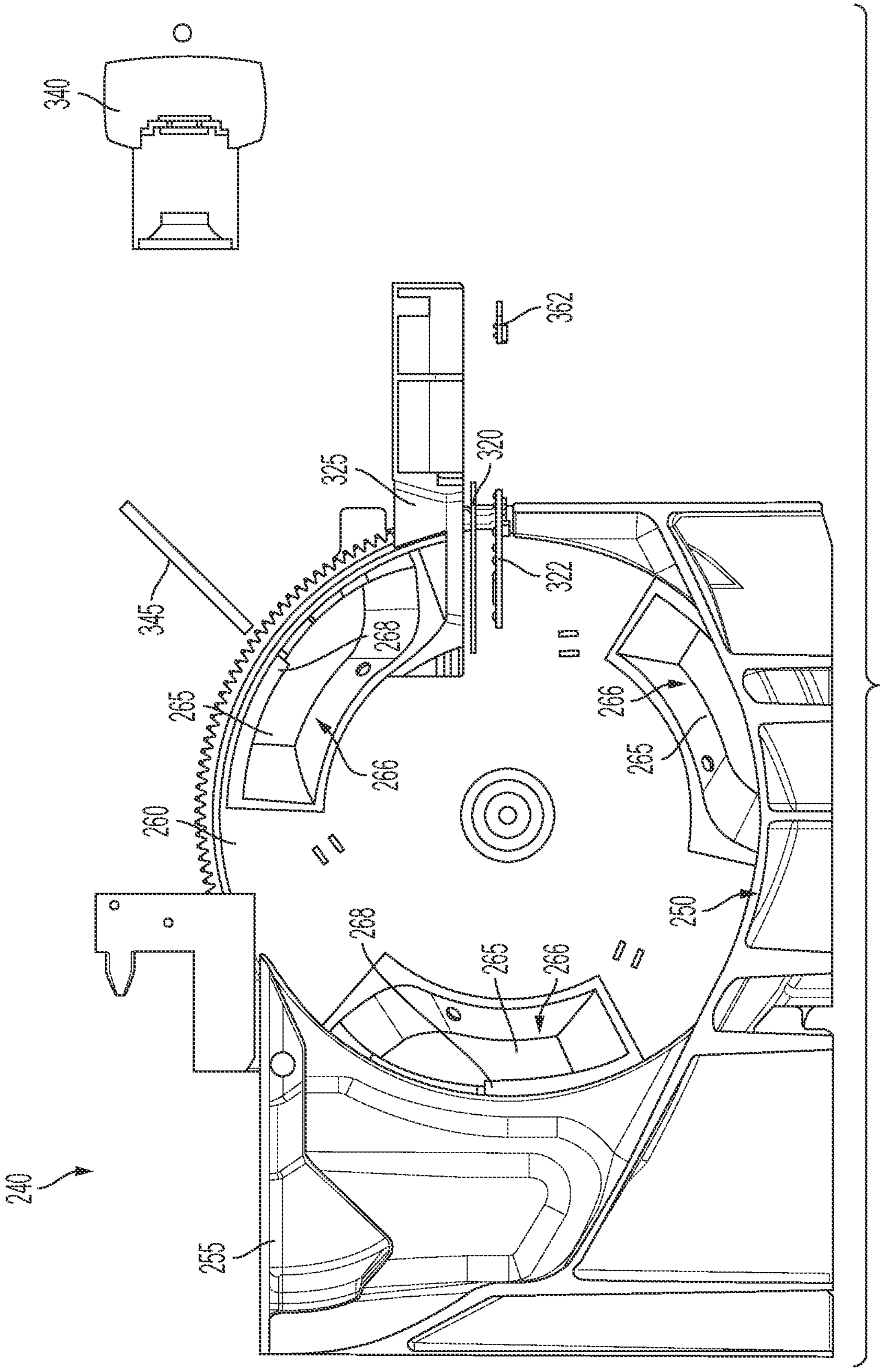
FIG. 9 is a cross-sectional view of the cartridge of FIG. 6 in accordance with some embodiments.
Figure 10:
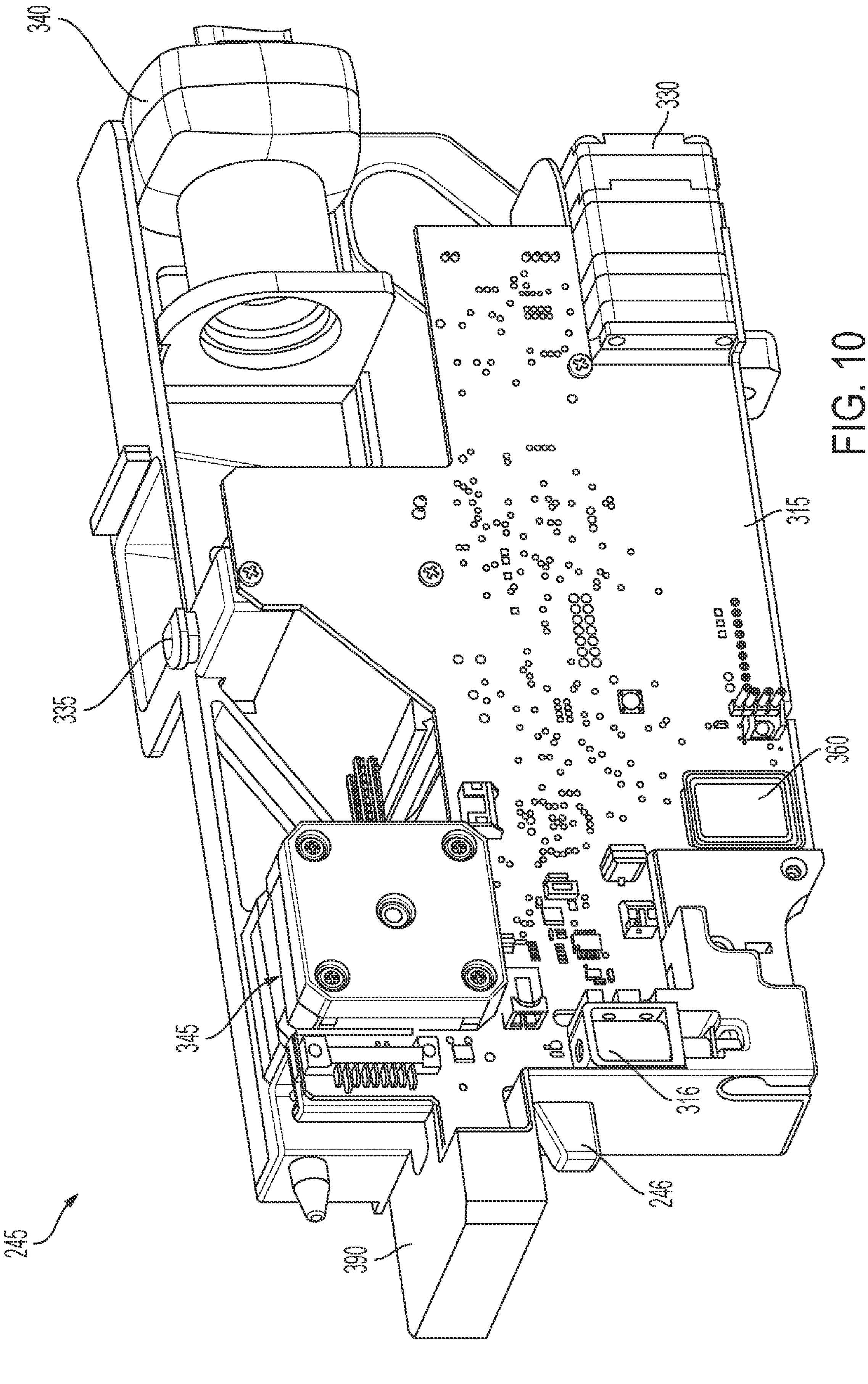
FIG. 10 is a perspective view of a cartridge mechanism of the universal feed cassette of FIG. 3 in accordance with some embodiments.
Figure 15:
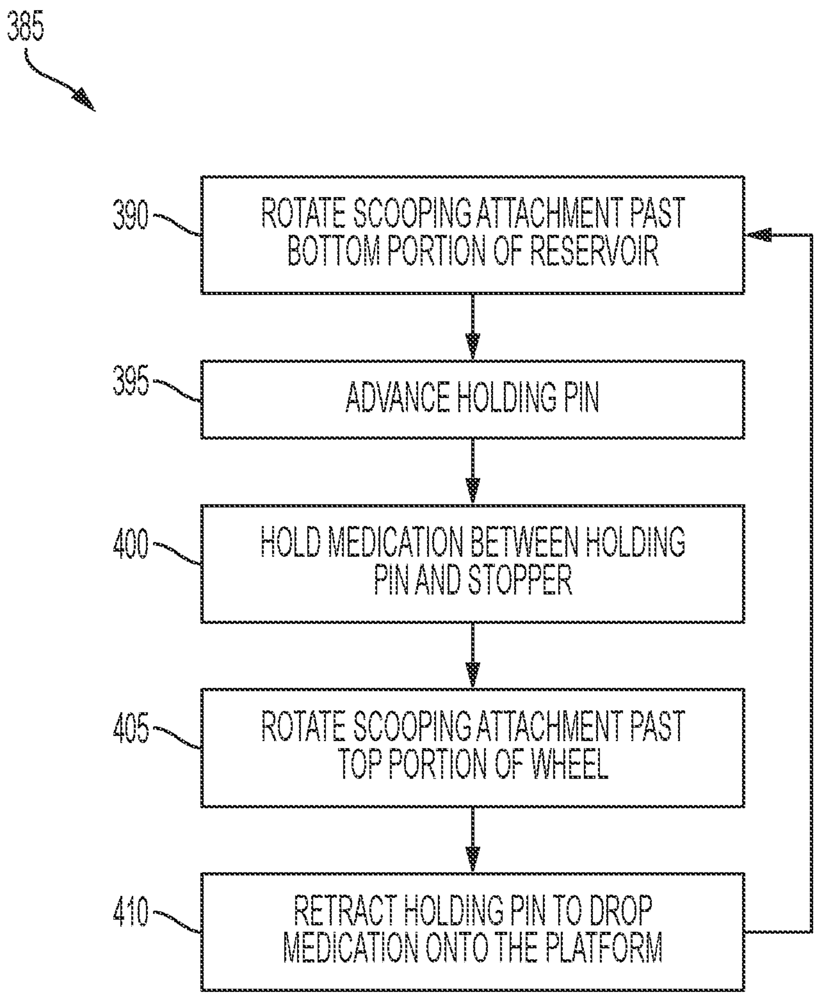
FIG. 15 is a flowchart of a method of delivering medications to a platform of the cartridge mechanism of FIG. 10 in accordance with some embodiments.

FIG. 15 is a flowchart illustrating one example method 385 of delivering medications to the platform 320. As illustrated in FIG. 15, the method 385 includes rotating, using the motor assembly 310, a scooping member 265 past the bottom portion of the reservoir 250 (at block 390). Referring to FIG. 9, when the scooping member 265 is at the bottom portion of the reservoir 250, the medications 180 move into the inward projection 266 of the scooping member 265 due to the curved shape of the reservoir 250. As the medications 180 move into the inward projection 266, the stopper 268 of the scooping member 265 carries at least one medication 180 past the bottom portion of the reservoir 250 as the scooping member 265 is rotated past the bottom portion of the reservoir 250. The scooping members 265 are placed within the wheel 260 along circumferential ends of the wheel 260. The wheel 260 is rotated to rotate the scooping members 265. As described above, teeth 275 of the wheel 260 interlock with teeth of the shaft 355, which is driven by the motor 350.

The method 385 also includes advancing, using the cam and follower mechanism 285, the holding pin 280 into the scooping member 265 (at block 395). Referring to FIGS. 7 and 9, as the scooping member 265 is rotated past the bottom portion of the reservoir 250, the follower 295 corresponding to the scooping member 265 encounters the arc portion 292 of the cam 290. The follower 295 is then advanced, which advances the holding pin 280 towards a circumference of the inward projection 266 of the scooping member 265.

The method 385 further includes holding the medication between the holding pin 280 and the stopper 268 (at block 400). When the holding pin 280 is advanced, a medication 180 is held between the holding pin 280, the circumferential end of the scooping member 265, and the stopper 268. The medication 180 is held in such a way until the scooping member 265 moves past the top portion of the wheel 260.

The method 385 also includes rotating, using the motor assembly 310, the scooping member 265 past the top portion of the wheel 260 (at block 405). As discussed above, the motor assembly 310 rotates the wheel 260 to rotate the scooping members 265. The motor assembly 310 may also include a position sensor (not shown) to detect a position of the wheel 260. For example, the motor assembly 310 may include a hall sensor to detect magnets placed at certain locations on the wheel 260 to determine the position of the wheel 260. In other embodiments, the position sensor may be an optical sensor or the like.

The method 385 further includes retracting, using the cam and follower mechanism 285, the holding pin 280 to drop the medication 180 on to the platform 320 (or for example, a verification system that verifies that an expected medication 180 (e.g., correct, single, and unbroken medication 180) is delivered) (at block 410). Referring to FIGS. 7 and 9, as the scooping member 265 is rotated past the top portion of the wheel 260, the follower 295 corresponding to the scooping member 265 encounters the cut-off portion 294 of the cam 290. The follower 295 is then retracted, which retracts the holding pin 280 away from the circumference of the inward projection 266 of the scooping member 265. As the holding pin 280 is retracted, the medication 180 drops from the scooping member 265 on to the platform 320. The scooping member 265 may be shaped to include a curved portion at a radially inward portion of the scooping member 265. The curved portion pushes the medication 180 away from the wheel 260 and onto the platform 320 when the medication 180 is released by the holding pin 280. Accordingly, the method 385 delivers a single medication 180 to the platform 320.

Figure 16:
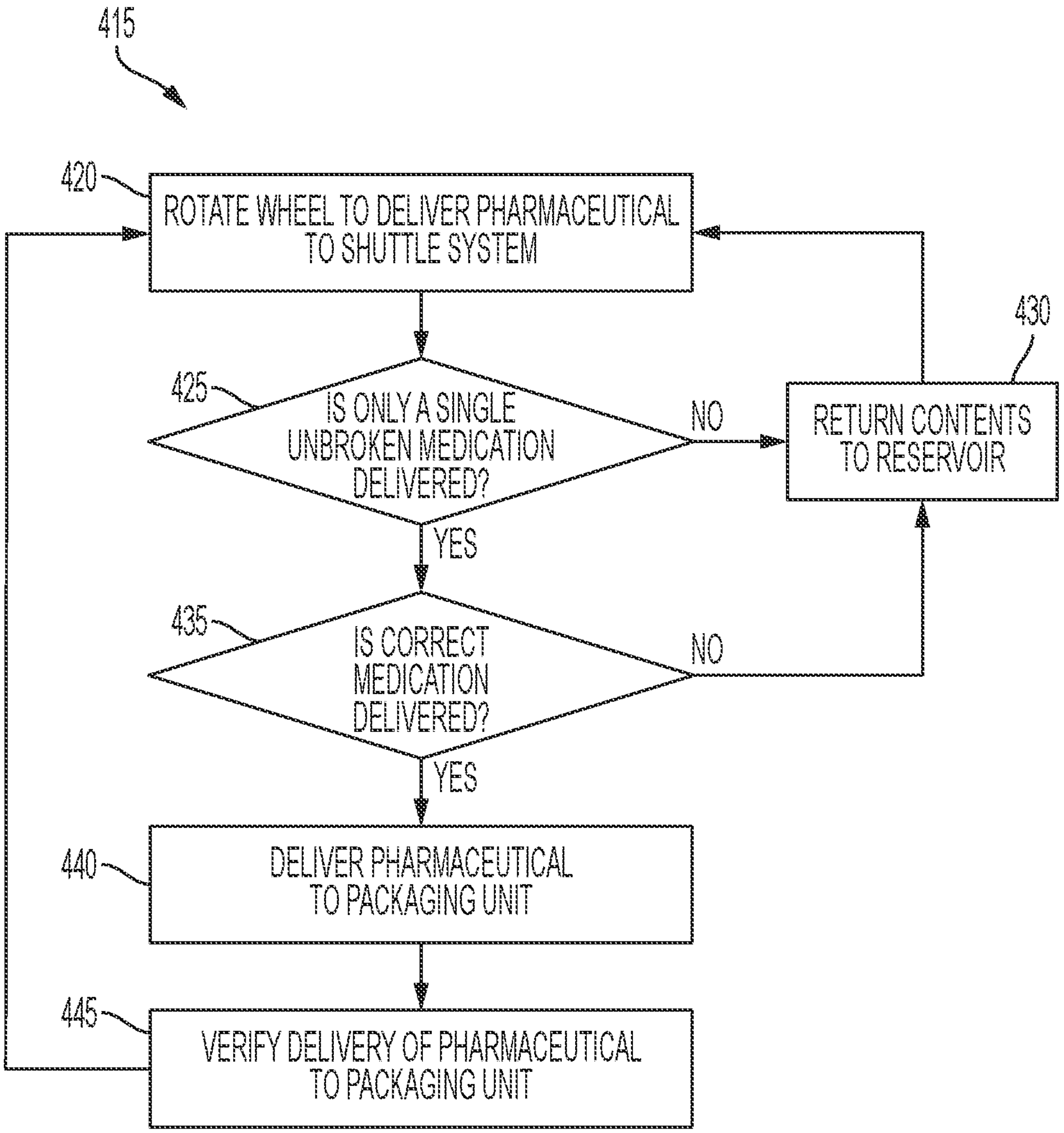
FIG. 16 is a flowchart of a method of dispensing medications from the cartridge of FIG. 6 in accordance with some embodiments.

FIG. 16 is a flowchart illustrating one example method 415 of dispensing medications from the cartridge 115. As illustrated in FIG. 16, the method 415 includes rotating the wheel 260 to deliver a medication 180 to the shuttle system 300 (at block 420). For example, the electronic processor 370 executes the method 385 of FIG. 15 to rotate the wheel and deliver the medication 180 to the shuttle system 300.

The automatic blister card packager 200 may pack only a single medication of a kind in any one blister compartment 120. Accordingly, the cartridge 240 may need to verify that an expected medication 180 (for example, a single unbroken medication 180) is dispensed to the packaging unit 210. The method 415 further includes determining whether only a single unbroken medication 180 is delivered to the shuttle system 300 (at block 425). This may also be referred to as singulation verification. The electronic processor 370 controls the camera system 305 to acquire an image of contents of the platform 320. The mirror 345 reflects the contents of platform 320 to the camera 340, which captures the image. The camera 340 provides the captured image to the electronic processor 370 for verification. The electronic processor 370 may use image recognition techniques on the captured image to ensure that only a single unbroken medication 180 is delivered to the shuttle system. Example image recognition techniques are described in U.S. Patent Application Publication No. 2018/0091745, the entire contents of which are hereby incorporated by reference.

When the electronic processor 370 determines that more than one medication 180 has been delivered to the shuttle system 300 or that a broken medication 180 has been delivered to the shuttle system 300, the method 415 includes returning the contents of the shuttle system 300 to the reservoir 125 (at block 430). The electronic processor 370 controls the shuttle drive 330 to move the shuttle 325 from the platform 320 to a first opening (e.g., the first position). The shuttle 325 returns the contents from the platform 320 to the reservoir 250 through the first opening. The method 415 returns to block 420 to deliver the next medication 180 to the shuttle system 300.

When the electronic processor 370 determines that only one unbroken medication 180 has been delivered to the shuttle system 300, the method 415 includes determining whether the correct medication 180 is delivered to the shuttle system 300 (at block 435). As described above, the electronic processor 370 may use the above incorporated image recognition techniques to determine whether the correct type of medication 180 has been delivered to the shuttle system 300.

When the electronic processor 370 determines that the incorrect type of medication 180 is delivered to the shuttle system 300, the method 415 moves to block 430 to return the contents of the shuttle system 300 to the reservoir 250, as described above. Accordingly, in blocks 410 and 420, the method 415 is determining whether an expected medication 180 is delivered to the shuttle system 300. In some embodiments, determining whether an expected medication 180 is delivered may include only one of the blocks 425 or 435 or the blocks 425 and 435 may be performed in a different order. In other embodiments, rather than checking for whether a single unbroken medication 180 is delivered to the shuttle system 300, determining whether an expected medication 180 may include determining whether a correct type of medication is delivered to the shuttle system 300 regardless of the number of medications delivered to the shuttle system 300. In yet other embodiments, determining whether an expected medication 180 may include determining whether a correct number of medications is delivered to the shuttle system 300.

When the electronic processor 370 determines that the correct type of medication 180 is delivered to the shuttle system 300, the method 415 includes delivering the medication 180 to the packaging unit 210 (at block 440). The electronic processor 370 controls the shuttle drive 330 to move the shuttle 325 from the platform 320 to a second opening (e.g., the second position). The shuttle 325 delivers the medication 180 from the platform 320 to the packaging unit 210 through the second opening, the conduit 335, and the dispensing opening.

The method 415 also includes verifying the delivery of the medication 180 to the packaging unit 210 (at block 445). The pill sensor 362 detects whether or not a pill was dispensed through the conduit 335 and provides indicating signals to the electronic processor 370. When the electronic processor 370 determines that a medication 180 was delivered to the packaging unit 210, the method returns to block 420 to deliver the next medication. When the electronic processor 370 determines that a medication 180 was not delivered to the packaging unit 210, the electronic processor 370 sends an interrupt to the control system of the automatic blister card packager 200 and returns to block 420 to re-deliver the medication 180.

An example cartridge 240 and cartridge mechanism 245 are described in U.S. Pat. No. 10,583,941, filed on Oct. 15, 2018, entitled "UNIVERSAL FEED MECHANISM FOR AUTOMATIC PACKAGER," the entire contents of which are hereby incorporated by reference Referring to FIG. 2, the automatic blister card packager 200 also includes a chute or manifold 230 and a blister card packaging unit 210. The universal feed cassette 205 is placed on top of the chute 230. The chute 230 includes a plurality of discrete tracks corresponding to each of the cartridges 240 (particularly, a conduit of each cartridge 240) mounted on the chute 230. The illustrated tracks are independent channels that together form the chute 230. The tracks direct pharmaceuticals from the universal feed cassette 205 toward packaging equipment 510 of the blister card packaging unit 210. Conduits of the cartridges 240 align with holes in the chute 230 such that medications slide down the chute 230 toward the packaging equipment 510. The tracks 450 isolate the medications from each other as the medications slide down the chute 230 toward the packaging equipment 510. In the illustrated embodiment, the chute 230 includes eight tracks 450. In other embodiments, the chute 230 may include fewer or more tracks 450. The number of tracks corresponds to the number of rows or columns (depending on the orientation) of a blister card that is desired to be filled. The automatic blister card packager 200 (and, thereby, the universal feed cassette 205 and the chute 230) may be designed with different numbers of cassettes and tracks to fill blister cards of different sizes.

Cameras are mounted at or near the junction of the conduits and the chute 230. Each camera is associated with one of the cartridge 240 supported in the universal feed cassette 205. The cameras are operable to determine whether the correct number and/or type of pharmaceuticals are being dispensed from the cartridges 240. In some embodiments, the cameras only look for the presence or absence of an object in the conduit. The cameras capture images of pharmaceuticals exiting the universal feed cassette 205 and compare features (e.g., color, contour, size, shape, inscription, etc.) of the pharmaceuticals to stored images of known pharmaceuticals. In some embodiments, recognition software may be employed to automatically compare the images captured by the cameras to stored images. In other embodiments, the captured images may be transmitted to a remotely-located pharmacist or technician who analyzes the images and verifies that the correct number and type of pharmaceuticals were dispensed. In further embodiments, the cameras may be infrared sensors that only detect whether an object (e.g., a pill) drops through the universal feed cassette 205, rather than identifying the particular type of pharmaceutical.

Figure 17:
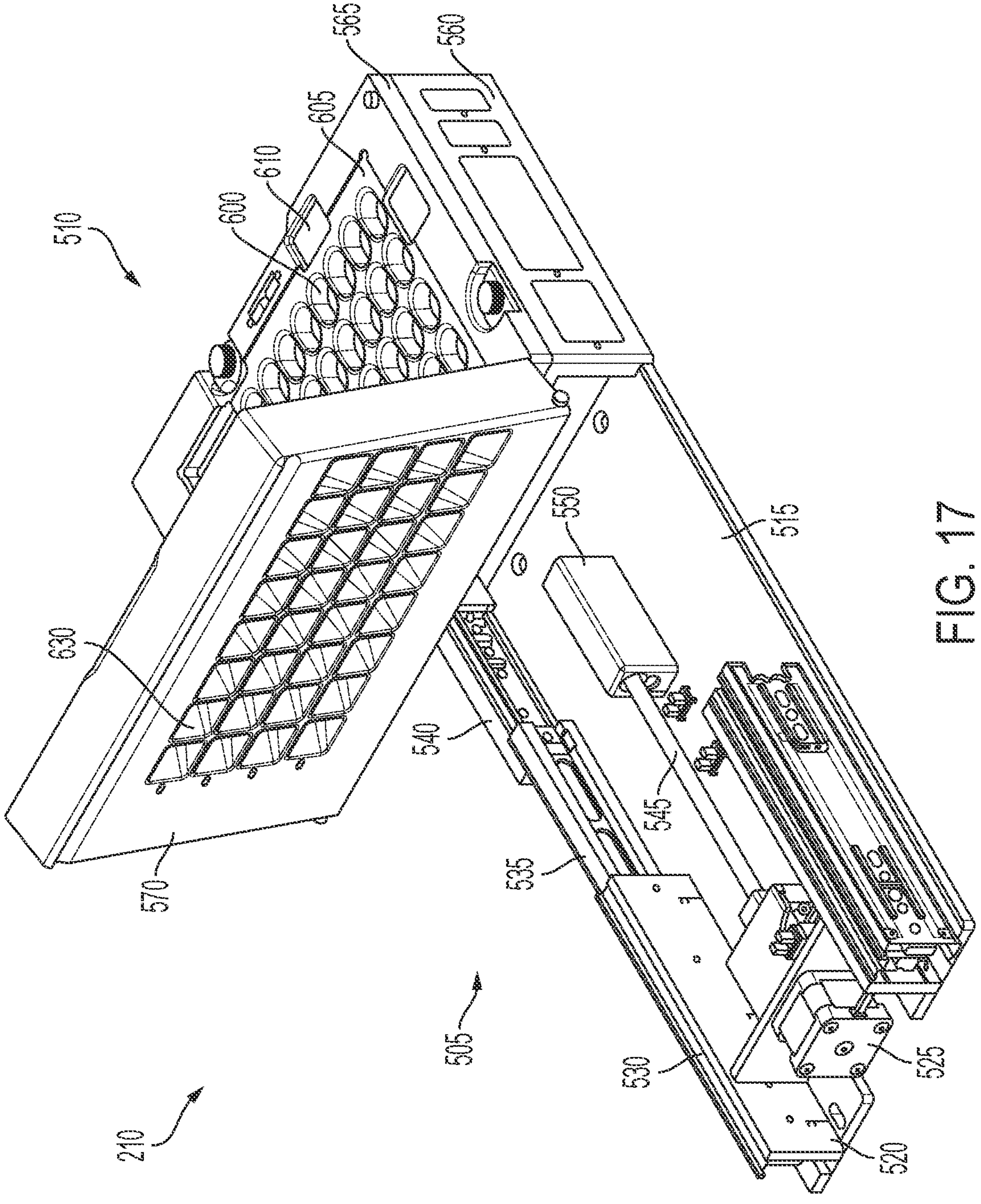
FIG. 17 is a perspective view of a packaging unit of the automatic blister card packager of FIG. 2 in accordance with some embodiments.
Figure 18A:
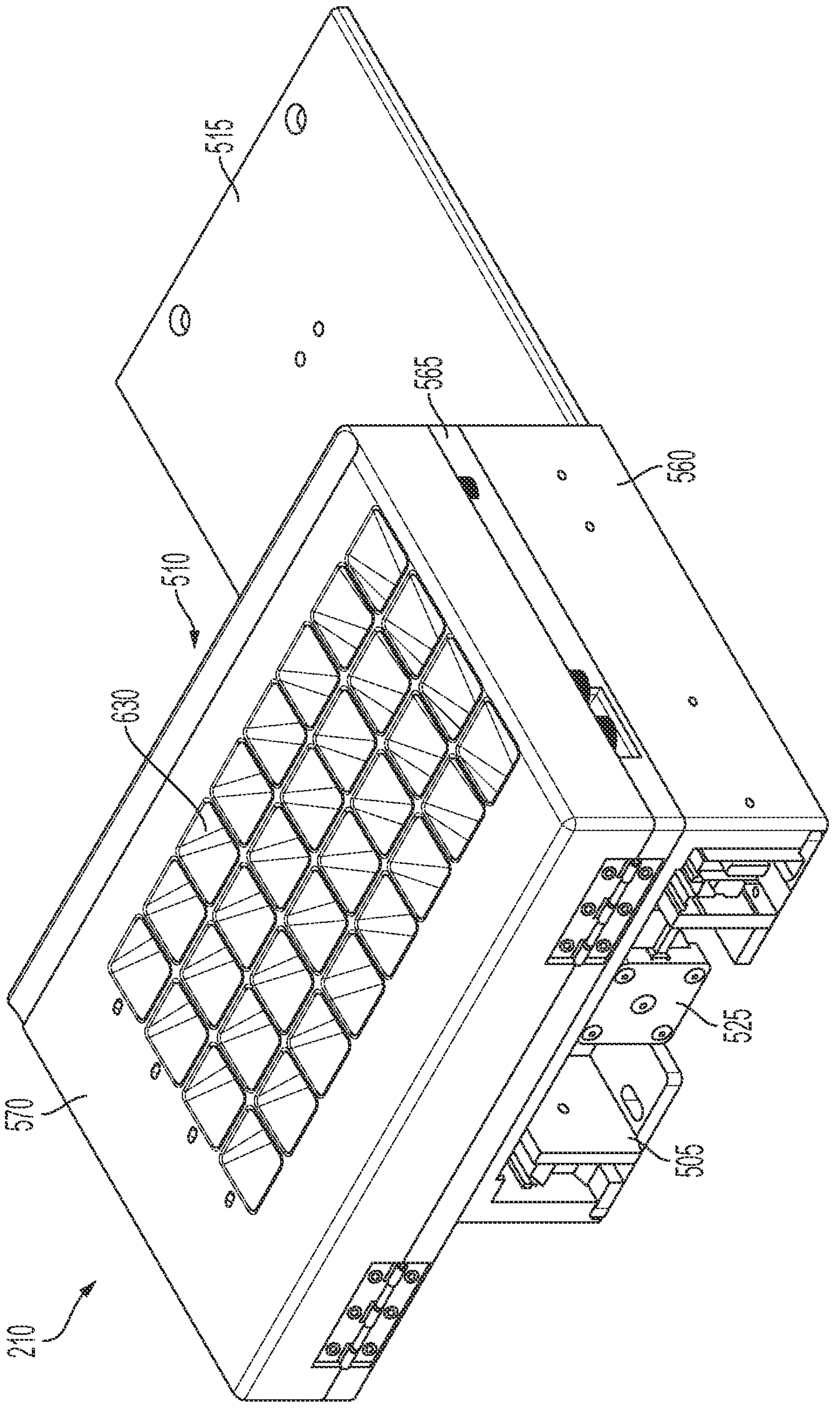
FIGS. 18A and 18B are perspective views of the packaging unit of FIG. 17 in accordance with some embodiments.
Figure 18B:
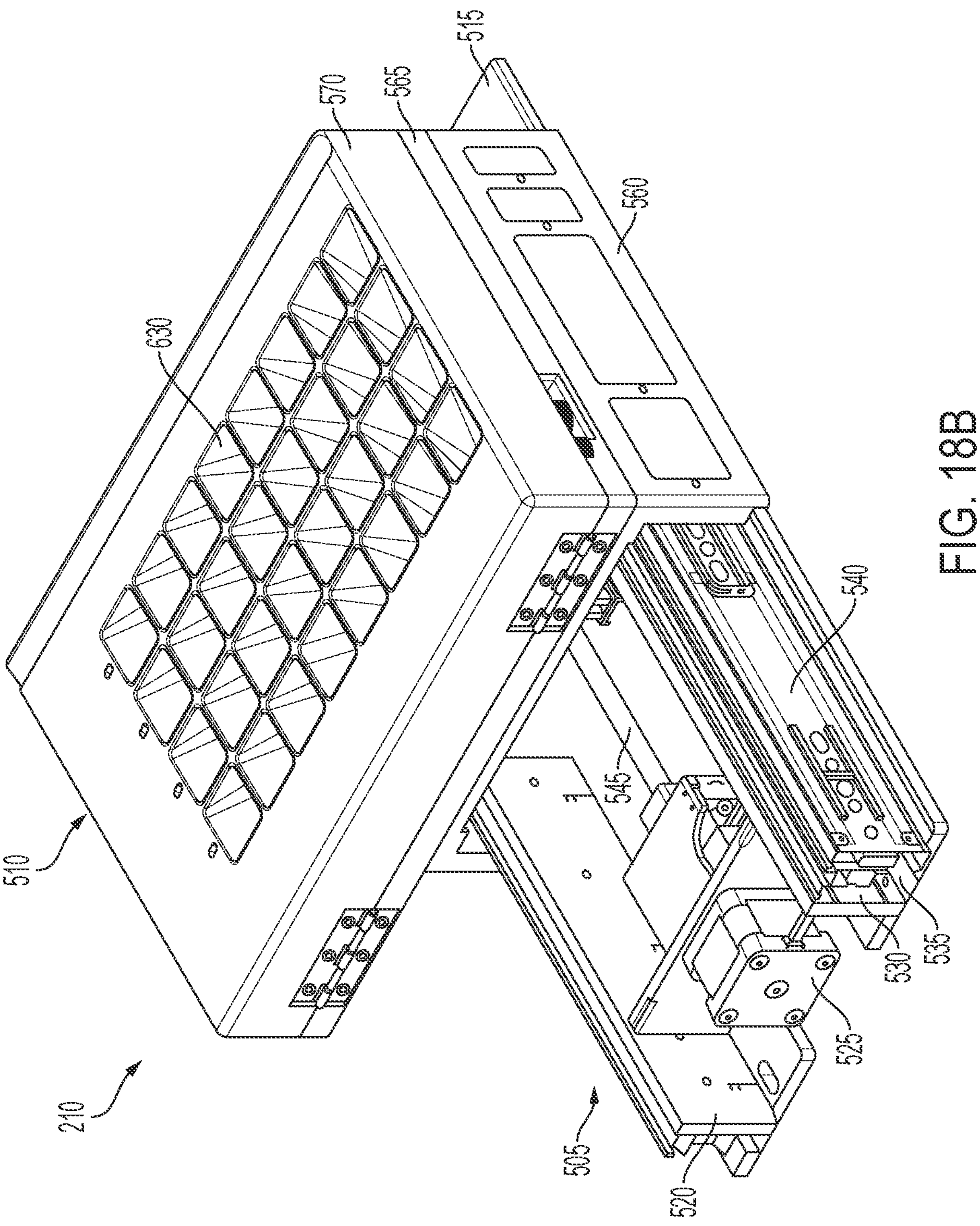

Referring to FIGS. 17-18B, the packaging unit 210 includes a rail system 505, and packaging equipment 510 (also referred to as a platen). The rail system 505 includes a rail base 515, rails 520, and a rail drive 525. The rail base 515 is fixed to a frame of the automatic blister card packager 200, for example, using fasteners. In some embodiments, the rail base 515 is removably secured to the frame such that a technician may remove the packaging unit 210 for servicing. The rails 520 are provided on the rail base 515.

In the example illustrated in FIGS. 17-18B, the rails 520 include fixed rails 530, first moveable rails 535, and second moveable rails 540. The fixed rails 530 are fastened to the rail base 515 using fasteners such that the fixed rails 530 are stationary with respect to the rail base 515. The fixed rails 530 start at a rear of the rail base 515 and extend, for example, up to a third of the length of the rail base 515. The first moveable rails 535 slide along the fixed rails 530 and extend the rails 520 up to two thirds of the length of the rail base 515. The second moveable rails 540 slide along the first moveable rails 535 and extend the rails 520 up to the entire length of the rail base 515. The packaging equipment 510 is attached to the second moveable rails 540 to move with the second moveable rails 540. The rails 520 telescope the packaging equipment 510 along the length of the rail base 515.

The rail drive 525 may be a motor assembly, an actuator, or the like that moves the packaging equipment 510 between the rear of the rail base 515 and the front of the rail base 515 along the length of the rail base 515. In the example illustrated, the rail drive 525 includes a rotating screw 545 that moves the packaging equipment 510 laterally between the rear of the rail base 515 and the front of the rail base 515 along the length of the rail base 515. The rotating screw 545 includes a magnetic end 550 at the end of the rotating screw 545. The magnetic end 550 attaches to a corresponding end 555 of the packaging equipment 510. The magnetic end 550 may include a magnet that attaches to magnetic material of the corresponding end 555. In some embodiments, the magnetic end 550 includes magnetic material that attaches to magnets 556 on or in the corresponding end 555. The rotating screw 545 moves the packaging equipment 510 between a first position (as shown in FIG. 18A) and a second position (as shown in FIG. 18B).

Referring to FIG. 18A, when in the first position, the packaging equipment 510 is within the automatic blister card packager 200 and is inaccessible by a pharmacist and/or technician. The rail drive 525 moves the packaging equipment 510 under the chute 230 within the automatic blister card packager 200 to fill a blister card 100 placed in the packaging equipment 510. The first position may correspond to a first third ($\frac{1}{3}^{rd}$) of the rail base 515 such that the packaging equipment 510 is entirely over the fixed rails 530 and can be moved by the rail drive 525 to align medication receiving openings 630 of the packaging equipment 510 with the chute 230.

Referring to FIG. 18B, when in the second position, the packaging equipment 510 may still be within the automatic blister card packager 200. However, at least a portion of the packaging equipment 510 is accessible by a user to pull the packaging equipment. The second position may correspond to a second third ($\frac{1}{3}^{rd}$) of the rail base 515 such that the first moveable rails 535 have travelled and reached an end of the fixed rails 530. When the rail drive 525 drives the rotating screw 545, the first moveable rails 535 move along the fixed rails 530 to move the packaging equipment 510 between the first position and the second position. When in the second position, a user may pull the packaging equipment 510 towards the user to disengage the packaging equipment 510 from the magnetic end 550. As such, a user may pull the packaging equipment from the second position to a third position (as shown in FIG. 17).

Referring to FIG. 17, when in the third position, the packaging equipment 510 is outside the automatic blister card packager 200. The third position may correspond to a final third ($\frac{1}{3}^{rd}$) of the rail base 515 such that the second moveable rails 540 have travelled and reached an end of the first moveable rails 535. When the user pulls the packaging equipment 510, the second moveable rails 540 slide along the first moveable rails 535 to move the packaging equipment 510 between the second position and the third position. When in the third position, the user may open the packaging equipment 510 to replace a filled blister card 100 from the packaging equipment.

Figure 19:
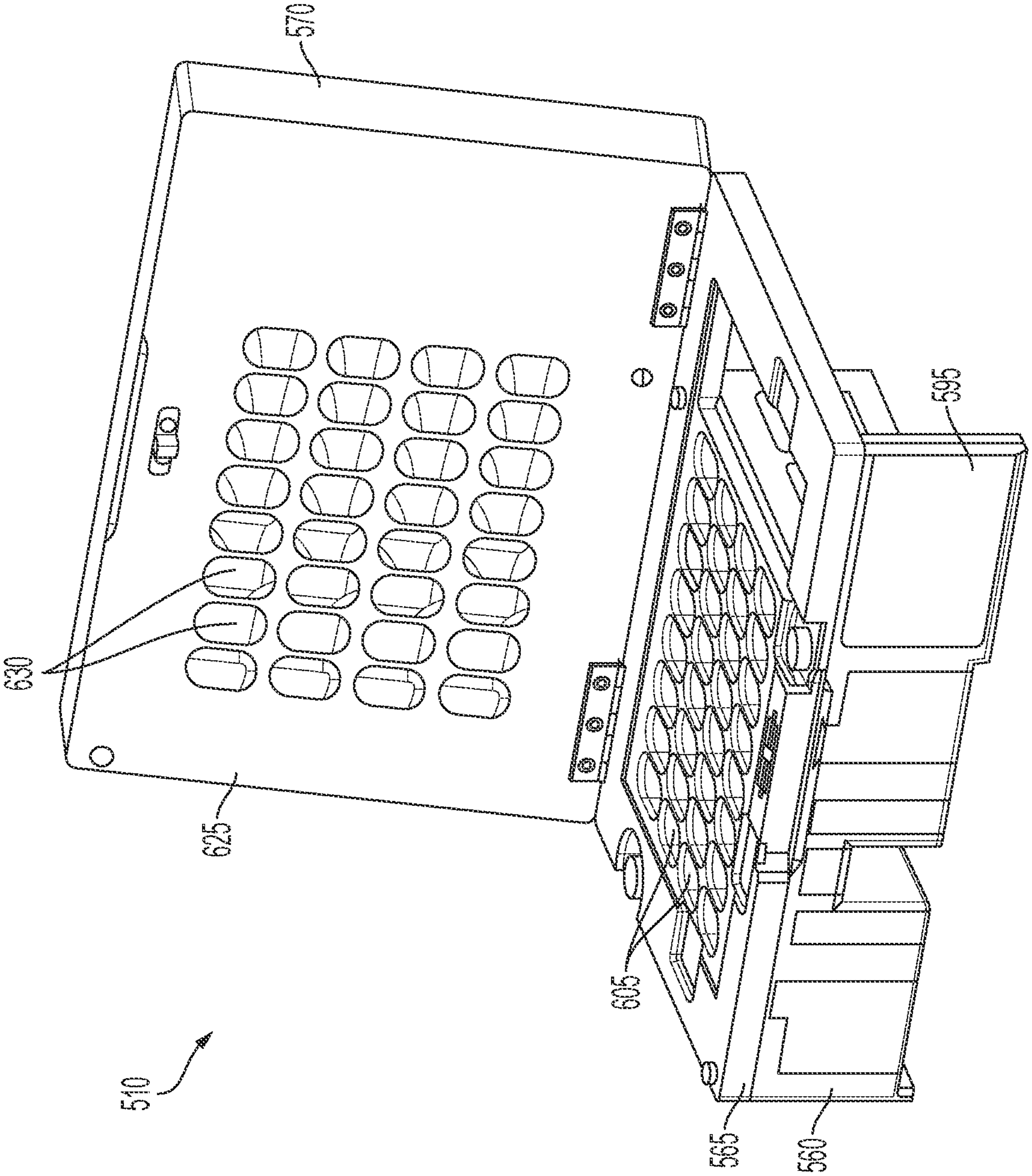
FIG. 19 is a perspective view of a packaging equipment of the packaging unit of FIG. 17 in accordance with some embodiments.
Figure 20A:
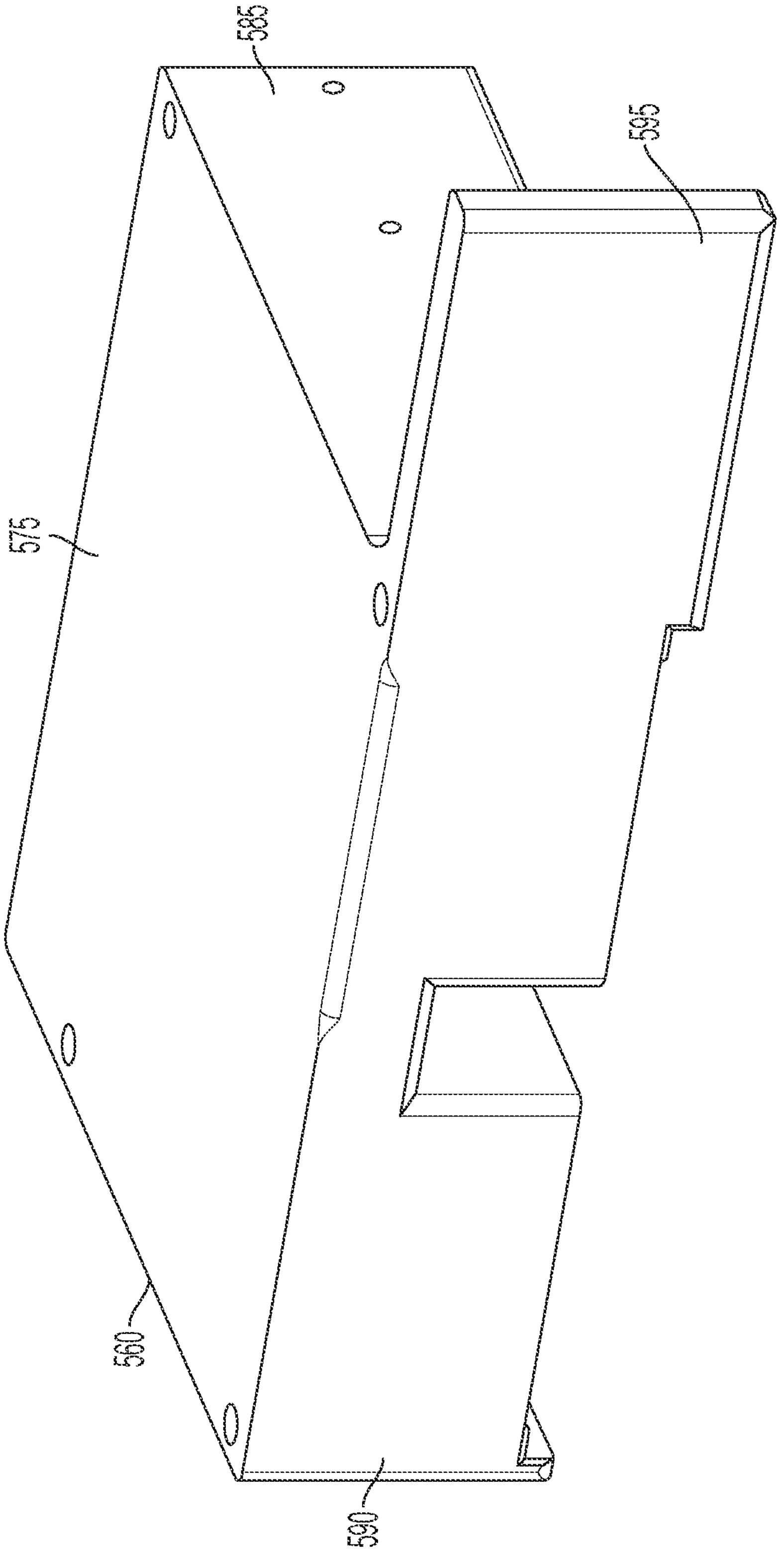
FIGS. 20A and 20B are perspective views of a packaging base of the packaging equipment of FIG. 19 in accordance with some embodiments.
Figure 20B:
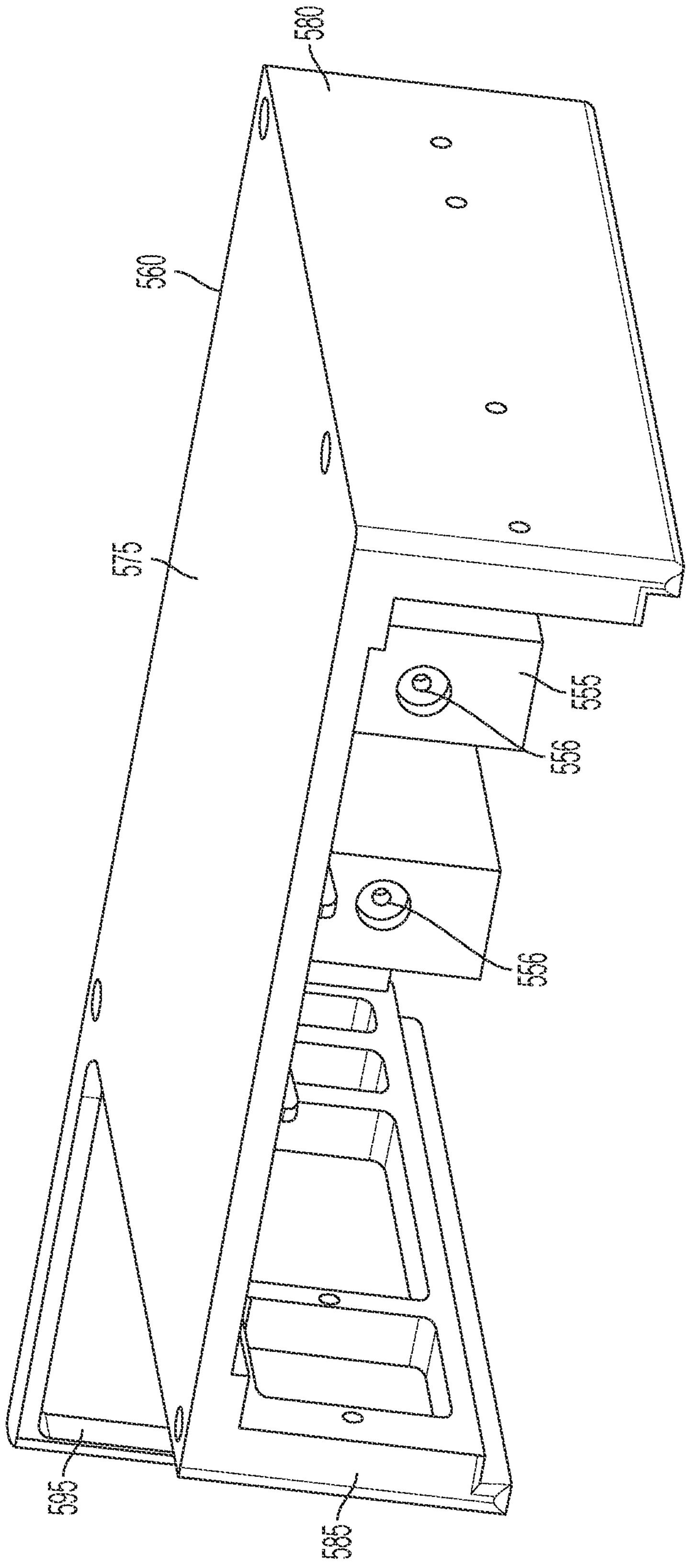

Referring to FIG. 19, the packaging equipment 510 includes a packaging base 560, a packaging plate 565, and a packaging lid 570. Referring to FIGS. 20A and 20B, the packaging base 560 includes a base portion 575, a first leg portion 580 extending downwards on a left side (e.g., a first side) of the base portion 575, a second leg portion 585 extending downwards on a right side (e.g., a second side) of the base portion 575, and a third leg portion 590 extending downwards on a front side (e.g., a third side) of the base portion 575. The rear side (e.g., a fourth side) of the base portion 575 is left open to accommodate the rail drive 525 under the packaging base 560. The first leg portion 580 is fastened to the second moveable rails 540 on the left side (e.g., the first side) and the second leg portion 585 is fastened to the second moveable rails 540 on the right side (e.g., the second side). The end 555 is provided on the third leg portion 590 and may include magnets 556 or magnetic material that correspondingly attaches to the magnetic end 550. The base portion 575 may also include a guard 595 provided on the second leg portion 585. The guard 595 may be provided at a front end of the packaging equipment and extends right of the second leg portion 585. The guard 595 inhibits a user's limbs or other objects from entering the inside of the blister card packager 200 during operation.

Figure 21:
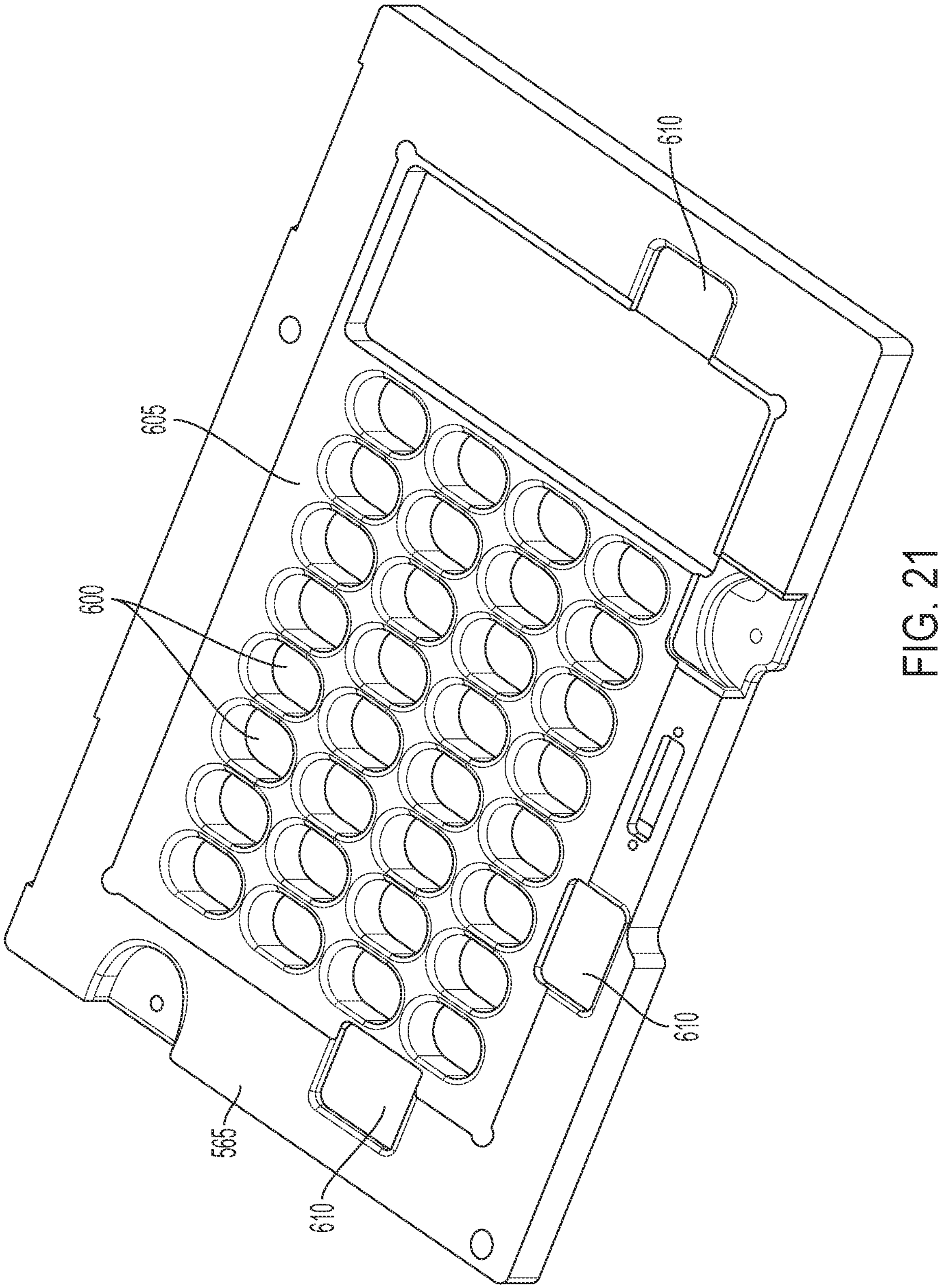
FIG. 21 is a perspective view of a packaging plate of the packaging equipment of FIG. 19 in accordance with some embodiments.

The packaging plate 565 is attached to the base portion 575 of the packaging base 560 such that the packaging plate 565 is above the packaging base 560. Referring to FIG. 21, the packaging plate 565 includes blister openings 600 provided in a blister card receiving portion 605. The blister card receiving portion 605 is slightly depressed in the packaging plate 565 to accommodate the blister sheet 110 when the packaging lid 570 is closed on the packaging plate 565. The blister openings 600 accommodate blister compartments 120 of the blister sheet 110. In the example illustrated, the blister openings 600 are through-holes that extend through the packaging plate 565. In some embodiments, the blister openings 600 do not extend through the packaging plate 565 and may include a base portion at the bottom of the opening. There are a limited number of manufacturers of blister cards 100. The variability in dimensions between different manufacturers of blister cards 100 is minimal with only up to 0.5 mm in variability in the height/width/depth of the blister compartments 120. Accordingly, the blister openings 600 may be designed to accommodate blister cards 100 from any manufacturer by dimensioning the blister openings 600 to fit a bigger of the blister cards 100 from different manufacturers. In some embodiments, different packaging plates 565 may be used for different facilities based on the blister cards 100 used by the facility that packages the blister cards 100.

The packaging plate 565 also includes pickup portions 610 that extend from the blister card receiving portion 605, for example, on opposite sides of the blister card receiving portion 605. When a blister card 100 is filled, a user may pick the blister card 100 from the packaging plate 565 by placing the user's fingers in the pickup portion 610. In some embodiments, only a single pickup portion 610 may be provided or the pickup portions 610 may be provided on the same side or adjacent sides of the blister card receiving portion 605. The pickup portions 610 may be depressed to similar depth or different depth than the blister card receiving portion 605 to facilitate picking up of a filled blister card 100.

Figure 22A:
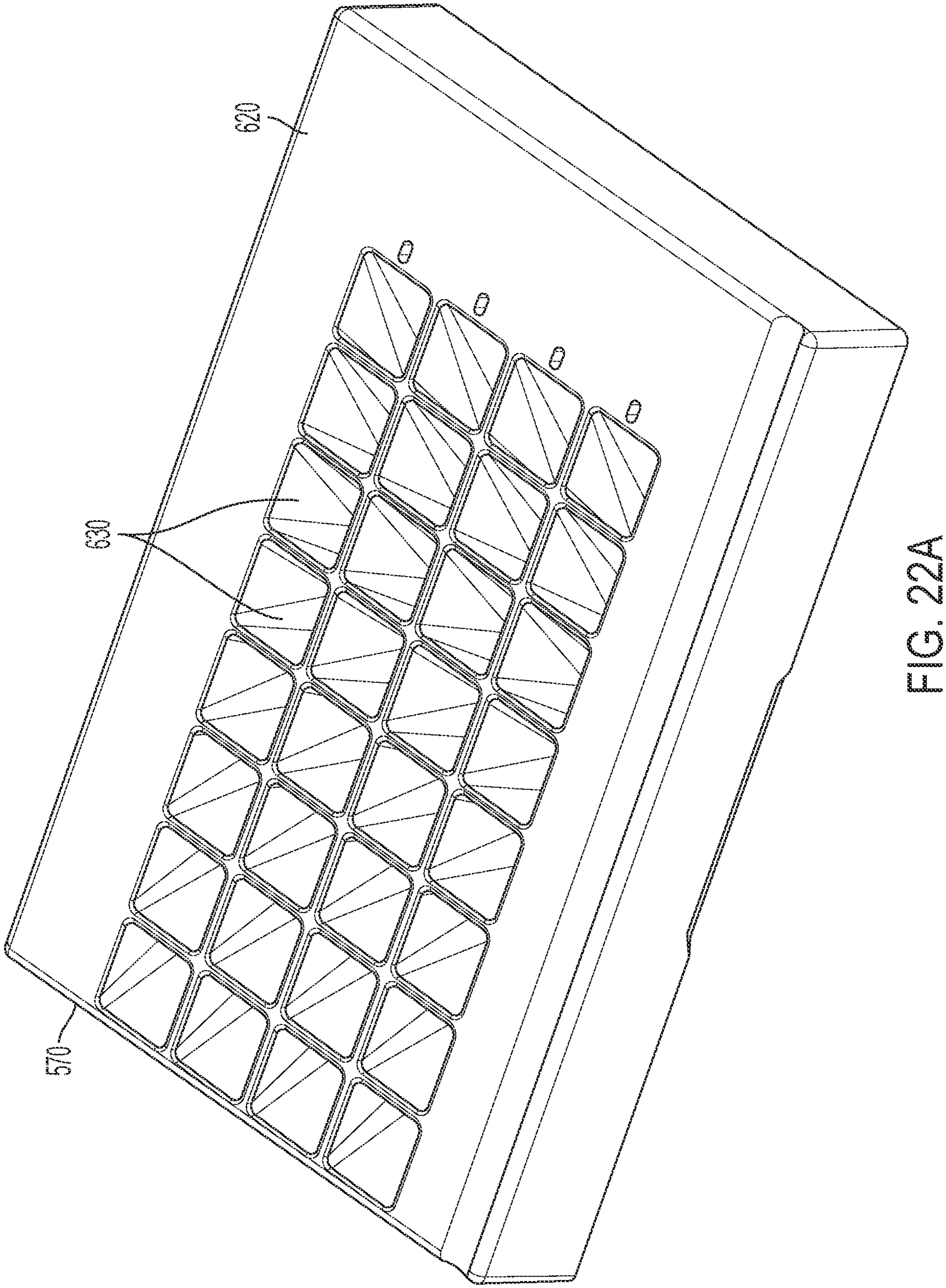
FIG. 22A is a perspective view of a packaging lid of the packaging equipment of FIG. 19 in accordance with some embodiments.
Figure 22B:
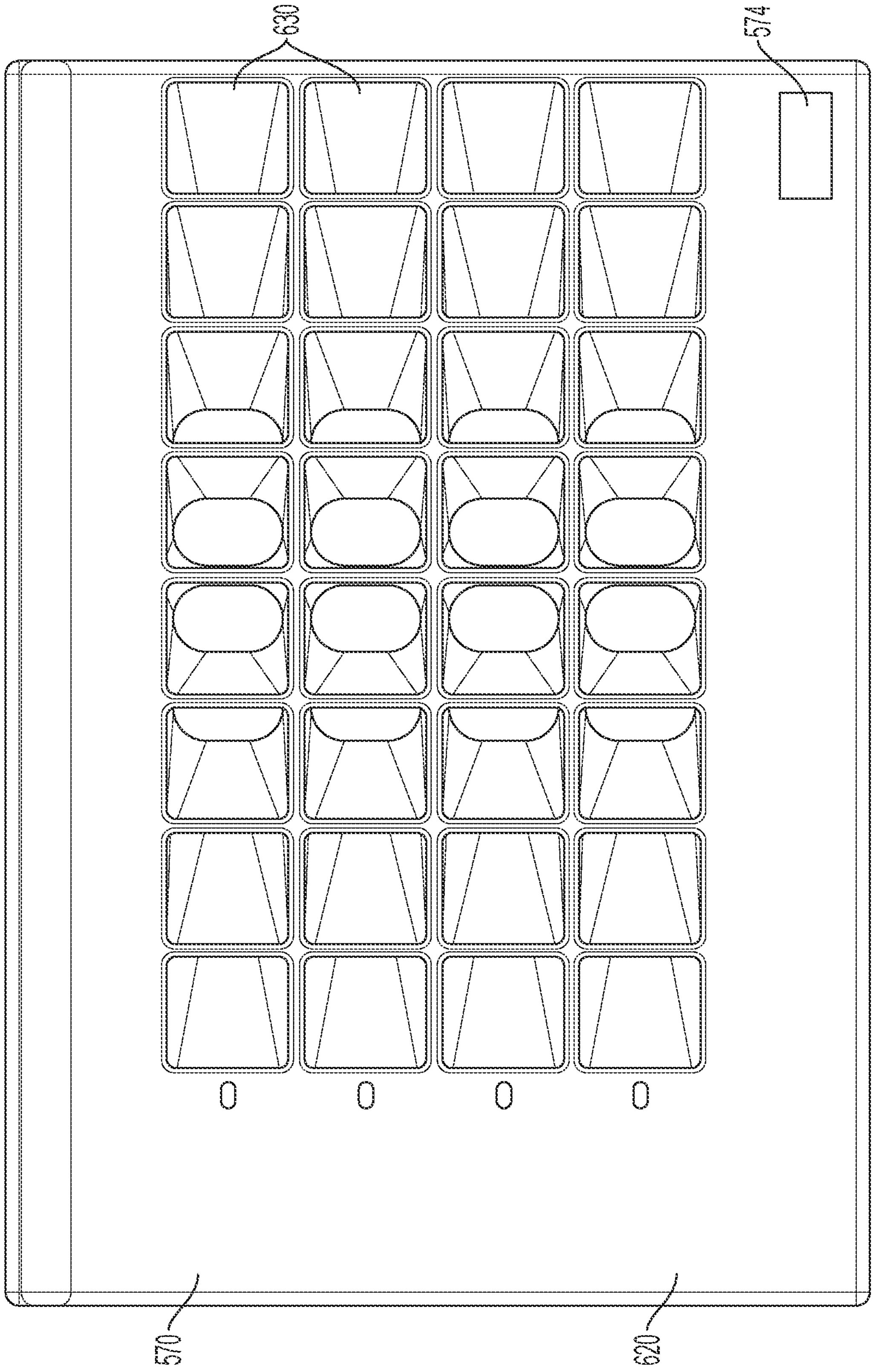
FIG. 22B is a top plan view of the packaging lid of FIG. 22A in accordance with some embodiments.
Figure 22C:
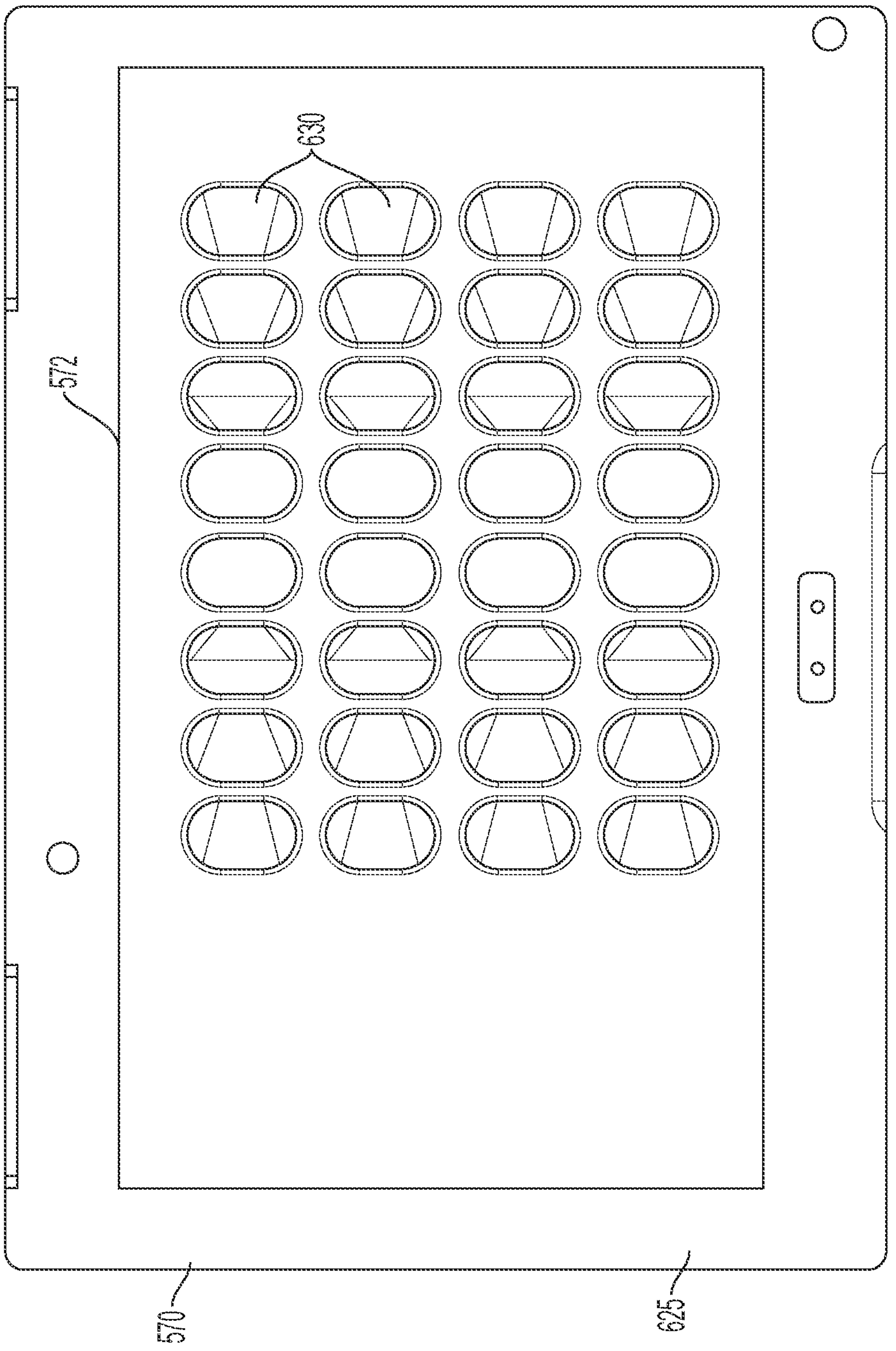
FIG. 22C is a bottom plan view of the packaging lid of FIG. 22A in accordance with some embodiments.

Referring to FIG. 19, the packaging lid 570 is hingedly connected to the packaging plate 565 using hinges 615. The hinges 615 are provided at a rear of the packaging equipment 510 such that the packaging lid 570 can be placed in a closed position and an open position. Referring to FIGS. 22A-22C, the packaging lid 570 includes a top side 620 and a bottom side 625 opposite the top side 620. Medication receiving openings 630 extend from the top side 620 to the bottom side 625 of the packaging lid 570. At the bottom side 625, the medication receiving openings 630 include a shape that corresponds to the blister openings 600 of the packaging plate 565. In the example illustrated, at the bottom side 625, the medication receiving openings 630 include a shape that has two straight sides and two curved sides. At the top side 620, the medication receiving openings 630 include a shape that corresponds to or accommodates medication dispensing openings in the chute 230. In the example illustrated, at the top side 620, the medication receiving openings 630 include a shape that is square or rectangular. The medication receiving openings 630 may have a larger area on the top side 620 compared to the area on the bottom side 625. Walls of the medication receiving openings 630 curve and/or converge between the shape on the top side 620 and the shape on the bottom side 625 to direct the medications from the chute 230 to the blister compartments 120 of the blister card 100 placed in the packaging plate 565. The medication receiving openings 630 are sized to inhibit medications from bouncing out of the packaging equipment 510. Particularly, the medication receiving openings 630 have a height to inhibit the medications from bouncing upwards and out of the top side 620 when dispensed from the chute 230. In some embodiments, the height of the medication receiving openings 630 is approximately 1 inch. In other embodiments, the height of the medication receiving openings 630 is between 1 inch and 2 inches. In further embodiments, the height of the medication receiving openings is between 2 inches and 3 inches. The added height of the medication receiving openings 630 also inhibits the medications from being sheared when the packaging equipment 510 moves into and out of the blister card packager 200.

In some embodiments, the packaging plate 565 and the packaging lid 570 are detachably attached to the packaging base 560. The packaging plates 565 and the packaging lids 570 may be provided in different sizes to accommodate blister cards 100 of different kinds, for example, from different manufacturers and/or having different sizes. In some embodiments, the packaging plates 565 and the packaging lids 570 may be provided in different sizes to accommodate manifolds or chutes having different sizes of medication dispensing openings. The packaging plate 565 and the packaging lid 570 can be detached from the base portion 560 to exchange with a packaging plate 565 and a packaging lid 570 of a different size.

The rail drive 525 moves the packaging equipment 510 to align the medication receiving openings 630 with the medication dispensing openings of the chute 230. When a new blister sheet 110 is placed in the packaging equipment 510, the rail drive 525 retracts the packaging equipment such that a first row of the medication receiving openings 630 (e.g., a front-most row of medication receiving openings 630) is aligned with the medication dispensing openings of the chute 230. When medication is dispensed from the chute to the blister compartments 120 of the first row, the rail drive 525 is actuated to move the packaging equipment 510 such that a second row of the medication receiving openings 630 is aligned with the medication dispensing openings of the chute 230. The rail drive 525 moves the packaging equipment 510 to successively align the rows of the medication receiving openings 630 with the medication dispensing openings of the chute 230. When the blister card 100 is filled, the rail drive 525 moves the packaging equipment 510 to the second position such that a user may replace the filled blister card 100 with an unfilled blister card 100.

In some embodiments, the blister card 100 may receive multiple medications in a single blister compartment 120. In these embodiments, a universal feed cassette 205 having multiple rows of cartridges 240 may be used. The universal feed cassette 205 may be stocked such that cartridges 240 including all the medications that are to be packaged in a single blister compartment 120 are provided in the same column. Cartridges 240 provided in the same column share the same track of the chute 230. Accordingly, when the universal feed cassette 205 is operated, the multiple medications that are to be received in the same blister compartment 120 are dropped together into the blister compartment 120 through the shared column. In some embodiments, the cartridges 240 including all the medications that are to be packaged in a single blister compartment 120 may be provided in different columns. In these embodiments, the rail drive 525 is operated to move the packaging equipment 510 around such that the blister compartments 120 are placed under different columns to receive the multiple medications.

As discussed above, when the packaging equipment 510 is in the second position, the user may pull the packaging equipment 510 to the third position to replace the blister card 100. When in the third position, the user may perform a first check or verification and observes the medication receiving openings 630 to ensure that no medications are stuck in the medication receiving openings 630 and that all the medications have transferred from the medication receiving openings 630 to the blister compartments 120 of the blister card 100 currently being filled. After the first check or verification, the user may open the packaging lid 570. When the packaging lid 570 is opened, the user may perform a second check or verification and observe the blister compartments 120 to ensure that the desired number of blister compartments 120 are correctly filled. The user may then place the label sheet 130 on the blister sheet 110 and press down to stick the label sheet 130 to the blister sheet 110. The label sheet 130 includes an adhesive to stick the label sheet 130 to the blister sheet 110. The user may then pick up the blister card 100 from the packaging plate 565 using the pickup portions 610. A new blister sheet 110 is then placed in the packaging plate 565 to fill the next blister card 100.

In some embodiments, a heating element 572 (shown in FIG. 22C) is provided on the packaging plate 565 and/or the packaging lid 570. A switch or push button 574 (shown in FIG. 22B) may be provided on the packaging lid 570 to activate the heating element 572. Once the user verifies that the blister compartments 120 are correctly are correctly filled, the user places the label sheet 130 on the blister sheet 110 and activates the heating element 572 by pushing the switch 574. The heating elements 572 provides the heat to heat seal the label sheet 130 to the blister sheet 110.

Figure 23:
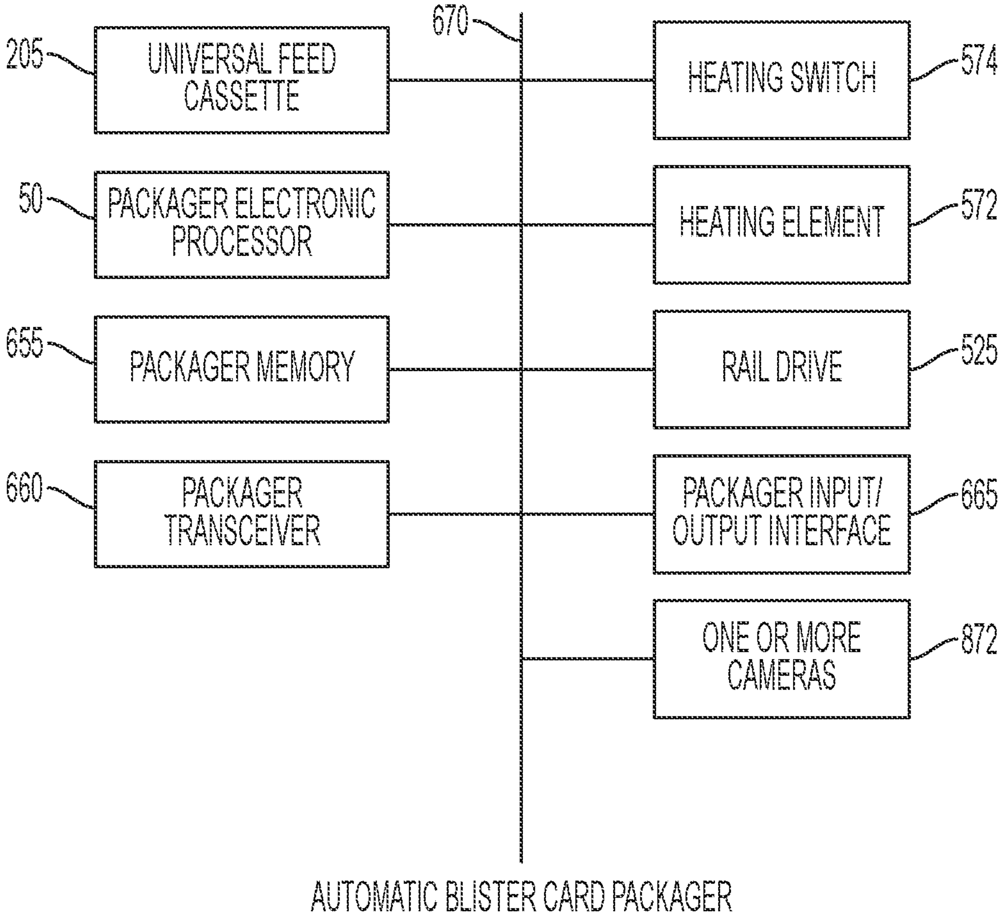
FIG. 23 is a block diagram of the automatic blister card packager of FIG. 2 in accordance with some embodiments.

FIG. 23 schematically illustrates one embodiment of the automatic blister card packager 200. The automatic blister card packager 200 controls operations of the rail drive 525 to align the packaging equipment 510 with the chute 230 as set forth above, and controls when the active cartridges 240 positioned on the chute 230 are operated.

In the example illustrated, the automatic blister card packager 200 includes a packager electronic processor 650, a packager memory 655, a packager transceiver 660, a packager input/output interface 665, and the rail drive 525. The packager electronic processor 650, the packager memory 655, the packager transceiver 660, the packager input/output interface 665, and the rail drive 525 communicate over one or more control and/or data buses (e.g., a communication bus 670). FIG. 23 illustrates only one exemplary embodiment of the automatic blister card packager 200. The automatic blister card packager 200 may include more or fewer components and may perform functions other than those explicitly described herein.

The packager electronic processor 650 and the packager memory 655 may be implemented similar to the electronic processor 370 and the memory 375 respectively, as described above. The packager transceiver 660 enables communication from the automatic blister card packager 200 to the communication network 675. In other embodiments, the packager transceiver 660 may include separate transmitting and receiving components, for example, a transmitter and a receiver. The automatic blister card packager 200, through the communication network 675, may communicate with the cartridge mechanism 245.

As noted above, the automatic blister card packager 200 may include the packager input/output interface 665 (or more commonly referred to as a user interface). The packager input/output interface 665 may include one or more input mechanisms (e.g., a touch screen, a keypad, a button, a knob, and the like), one or more output mechanisms (e.g., a display, a printer, a speaker, and the like), or a combination thereof. The packager input/output interface 665 receives input from the input devices actuated by a user, and provides output to the output devices with which a user interacts. In some embodiments, as an alternative or in addition to managing inputs and outputs through the packager input/output interface 665, the automatic blister card packager 200 may receive user inputs, provide user outputs, or both by communicating with an external device, such as a console computer, over a wired or wireless connection.

Figure 24:
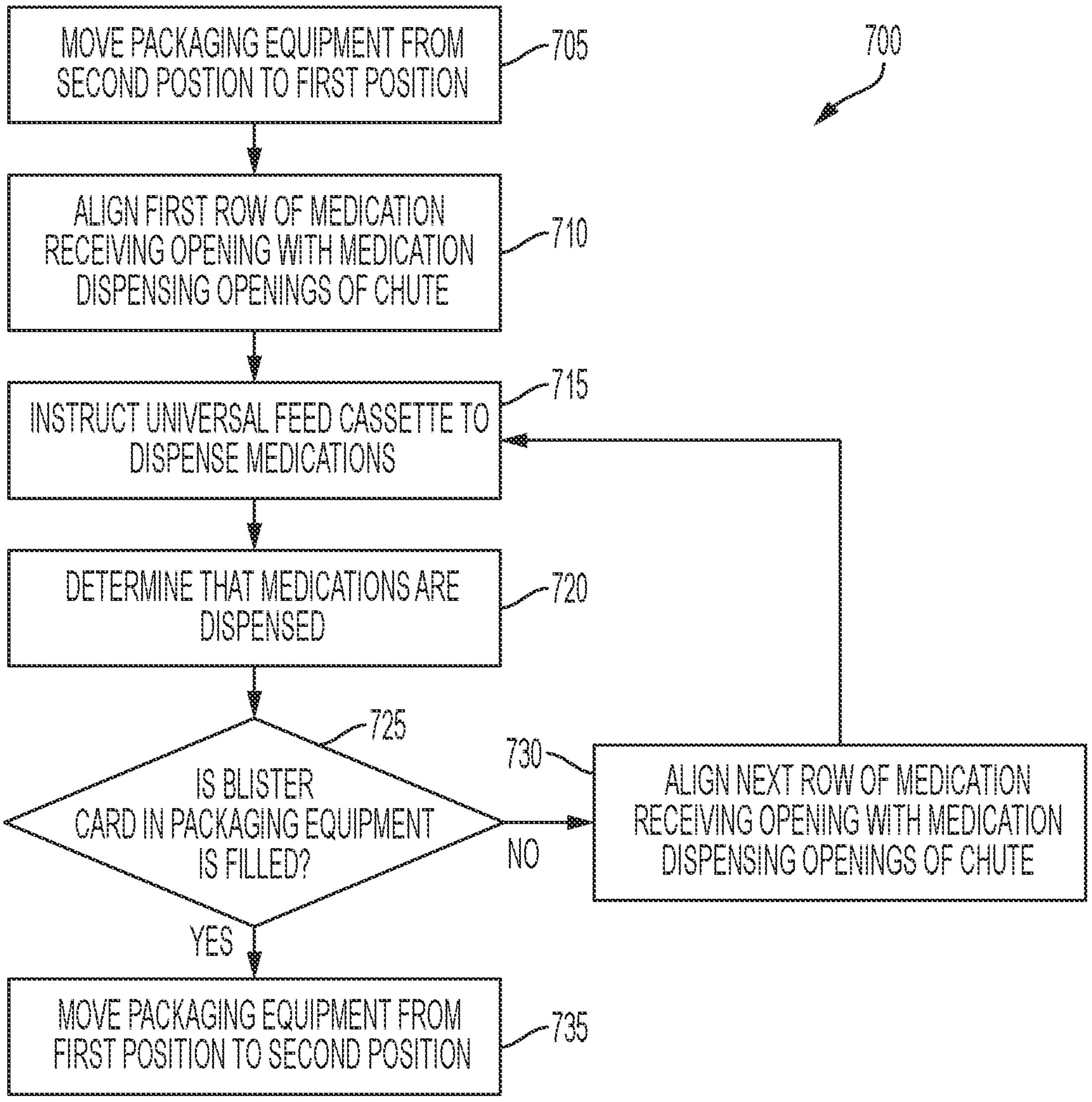
FIG. 24 is a flowchart of a method for packaging a blister card using the automatic blister card packager of FIG. 2 in accordance with some embodiments.
Figure 25:
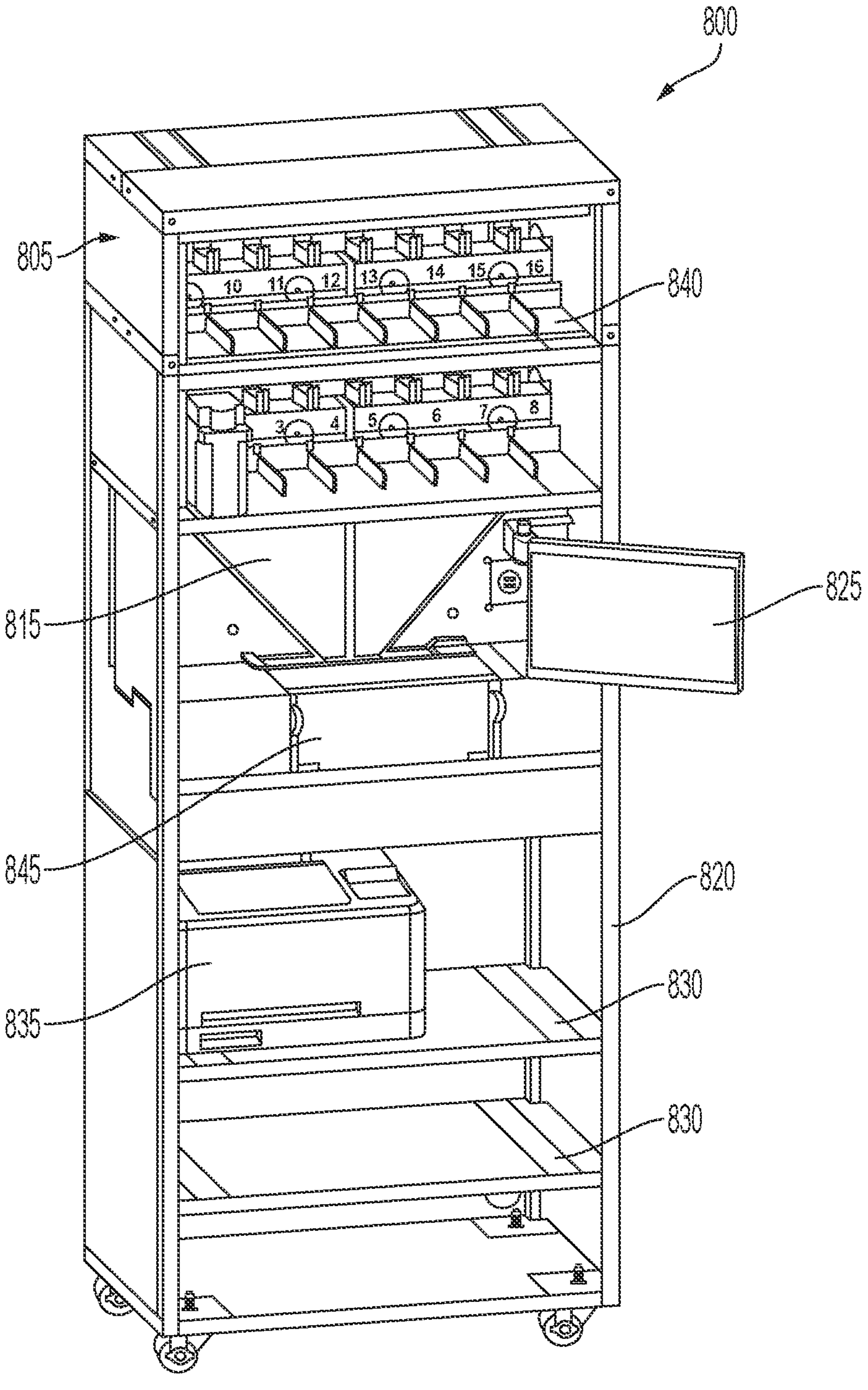
FIG. 25 is a perspective view of another automatic blister card packager in accordance with some embodiments.

FIG. 24 is a flowchart illustrating one example method 700 of packaging blister cards 100. As illustrated in FIG. 24, the method 700 includes moving, using the rail drive 525, the packaging equipment 510 from the second position to the first position (at block 705). The packager electronic processor 650 controls the rail drive 525 to move the packaging equipment 510 from the second position to the first position as set forth above. A user places an unfilled blister sheet 110 in the packaging equipment and pushes the packaging equipment 510 from the third position to the second position such that the end 555 attaches to the magnetic end 550. In some embodiments, the packager electronic processor 650 may determine that the end 555 is attached to the magnetic end 550 and in response controls the rail drive 525 to move the packaging equipment from the second position to the first position.

The method 700 also includes aligning, using the rail drive 525, a first row of the medication receiving openings 630 with the medication dispensing openings of the chute 230 (at block 710). The packager electronic processor 650 controls the rail drive 525 to align the first row, for example, the front-most row of the medication receiving openings 630 with the medication dispensing openings of the chute 230. The method 700 further includes instructing the universal feed cassette 205 to dispense medications (at block 715). The universal feed cassette 205 controls the individual cartridge mechanism 245 to dispense medications to the packaging equipment 510 through the chute 230.

The method 700 also includes determining, using the packager electronic processor 650, that medications are dispensed (at block 720). The packager electronic processor 650 may determine that the medications are dispensed based on receiving an acknowledgement from the universal feed cassette 205. In some embodiments, the packager electronic processor 650 may implement a timer and determine that the medications are dispensed when the timer expires. In some embodiments, the packager electronic processor 650 uses the cameras or sensors placed near the conduits of the chute 230 to determine that a medication passed through the chute 230. The method 700 further includes determining, using the packager electronic processor 650, whether a blister card 100 in the packaging equipment 510 is filled (at block 725). The packager electronic processor 650 may determine that the blister card 100 is filled when the medications are dispensed to the last row of the medication receiving openings 630.

When the packager electronic processor 650 determines that the blister card 100 has not yet been filled, the method 700 includes aligning, using the rail drive 525, a next row of the medication receiving openings 630 with the medication dispensing openings of the chute 230 (at block 730). The packager electronic processor 650 controls the rail drive 525 to align the next row, for example, the second, the third, or the fourth row of the medication receiving openings 630 with the medication dispensing openings of the chute 230. In some embodiments, the electronic processor 650 implements a delay before aligning the next row. The delay may be selected to account for settling of the medication (e.g., after bouncing) in the blaster card 100. The method repeats blocks 715, 720, 725, and 730 until the blister card 100 is filled. When the packager electronic processor 650 determines that the blister card 100 has not yet been filled, the method 700 includes moving, using the rail drive 525, the packaging equipment 510 from the first position to the second position (at block 735). The packager electronic processor 650 controls the rail drive 525 to move the packaging equipment 510 from the first position to the second position as set forth above. The user then replaces filled blister card 100 with the next blister card 100 to be filled.

In some embodiments, the chute 230 may include two or more rows of medication dispensing openings such that more than one row of the blister compartments 120 can be simultaneously filled. In one embodiment having two rows of medication dispensing openings, a first row of medication dispensing openings draws medications from a first row of cartridges 240, and a second row of medication dispensing openings draws medications from a second row of cartridges 240. In this embodiments, the first row of medications dispensing openings may be used to fill the blister cards 100 while the second row of cartridges 240 is being refilled, and the second row of medications dispending openings may be used to fill the blister cards 100 while the first row of cartridges 240 are being refilled. Additionally, the first row of cartridges 240 may be used for a first medication and the second row of cartridges 240 may be used for a second medication, and so on, when the blister card 100 is being packaged with multiple medications. In one embodiment having four rows of medication dispensing openings drawing medications from four rows of cartridges 240, all four rows of medication dispensing openings may be used to quickly fill the blister card 100 in one go.

Although the illustrated packaging equipment 510 is moved linearly between positions by the rail drive 525, in other embodiments, the packaging equipment 510 may be moved in other manners and/or by other suitable means. For example, the packaging equipment 510 may be mounted on a plate (e.g., a turn-style plate) that is rotatable between positions. Alternatively, the packaging equipment 510 may be connected to a conveyor- or chain-style system that moves the packaging equipment 510 in a loop (e.g., forward and backward, and up and down). In such embodiments, the automatic blister card packager 200 may include more than one packaging equipment. For example, the automatic blister card packager 200 may include two packaging equipments, such that as one packaging equipment on one side of the turn-style plate or the conveyor-style system is being filled by the automatic blister card packager 200, the other packaging equipment on an opposite side of the turn-style plate or the conveyor-style system can be manipulated (e.g., inspected, opened/closed, refilled, etc.) by a user.

FIGS. 25-31 illustrate another example of an automatic blister card packager 800. The automatic blister card packager 800 is similar to the automatic blister card packager 200 described above with reference to FIGS. 1-24. Reference is made to the description of the automatic blister card packager 200 for description of features, operations, and alternatives of the automatic blister card packager 800 not explicitly described below. It should be noted that features of the automatic blister card packager 200 may be used with the automatic blister card packager 800 and vice versa.

The illustrated automatic blister card packager 800 includes a universal feed cassette 805, a blister card packaging unit 810 (FIGS. 26-30), and a manifold 815 that connects the universal feed cassette 805 and the packaging unit 810. The universal feed cassette 805 and the packaging unit 810 are supported by a frame 820. The frame 820 also supports a screen 825. The screen 825 provides a user interface for interacting with the automatic blister card packager 800. In some embodiments, the screen 825 may be a touch screen. In other embodiments, the automatic blister card packager 800 may include other devices for the user interface, such as a mouse, trackball or trackpad, keyboard, camera, speaker, microphone, and the like. The frame 820 further includes shelves 830 for supporting other devices associated with the automatic blister card packager 800, such as a printer 835. As such, the automatic blister card packager 800 may be a standalone unit.

In the illustrated embodiment, the universal feed cassette 805 includes sixteen cartridge slots 840. The cartridge slots 840 are configured to receive cartridges, such as the cartridges 240 shown in FIG. 6. The illustrated cartridge slots 840 are arranged in two vertically-stacked rows of eight. In other embodiments, the universal feed cassette 805 may include fewer or more cartridge slots 840, as noted above. In one example, the universal feed cassette 805 may include twenty cartridge slots 840. The cartridge slots 840 are arranged in two vertically-stacked rows of ten. In another example, the universal feed cassette 805 includes a single row of 10 cartridge slots 840. These universal feed cassettes 805 with ten or twenty cartridge slots 840 can be used to fill blister cards 120 having a 10×6 blister compartment 120 configuration.

Figure 26:
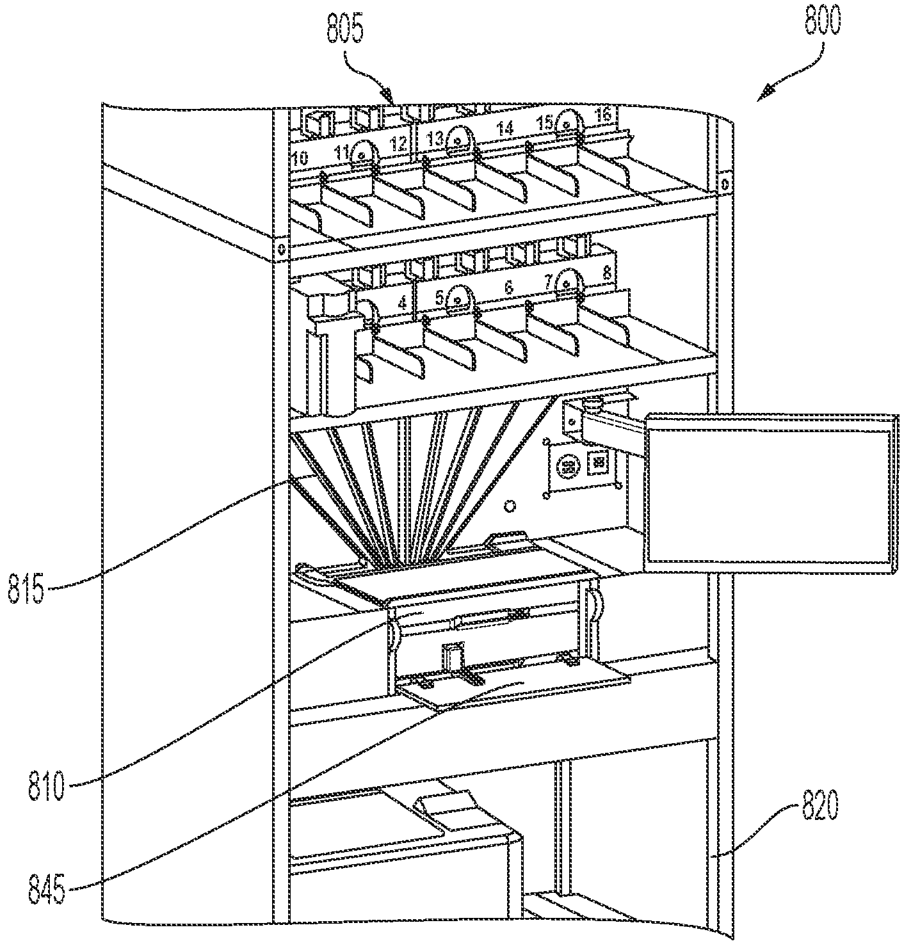
FIG. 26 is an enlarged view of a portion of the automatic blister card packager of FIG. 25, illustrating a door in an open position and a blister card packaging unit in a first position.

As shown in FIG. 26, the automatic blister card packager 800 includes a door 845 that provides selective access to the packaging unit 810. The door 845 is movable between a closed position (FIG. 25) and an open position (FIG. 26). In the illustrated embodiment, the door 845 pivots between the closed and open positions. When in the open position, the door 845 may also provide a shelf to help support the packaging unit 810.

Figure 27:
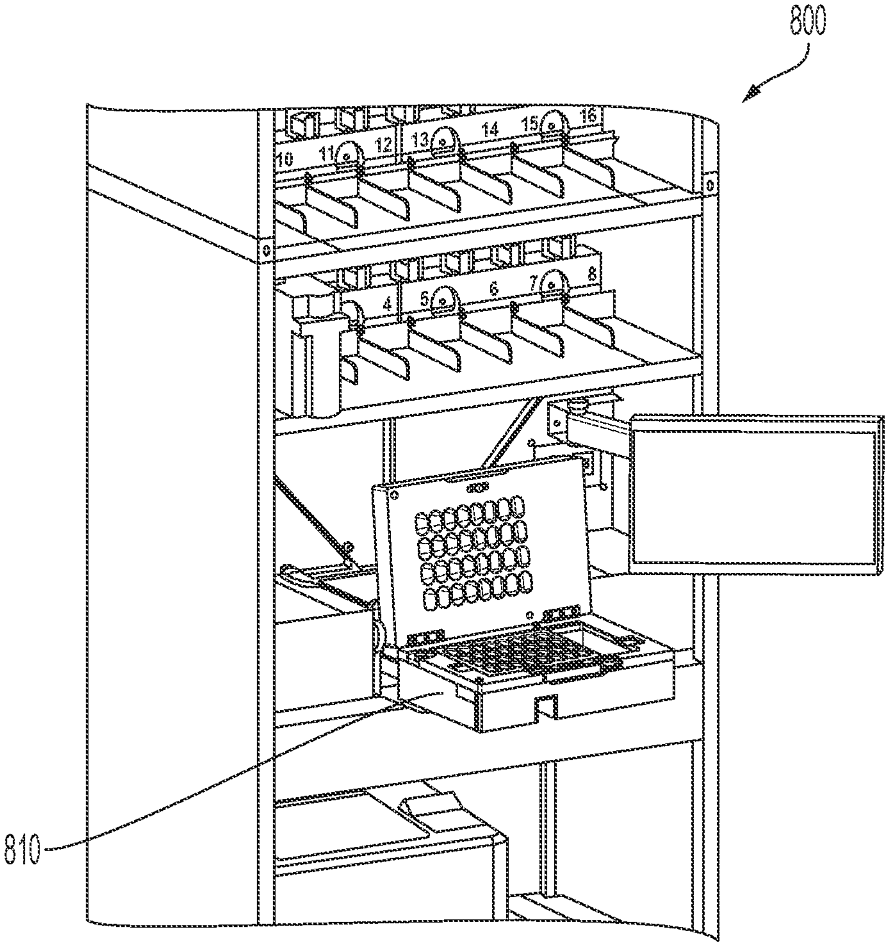
FIG. 27 is an enlarged view of a portion of the automatic blister card packager of FIG. 25, illustrating the blister card packaging unit in a second position.
Figure 28:
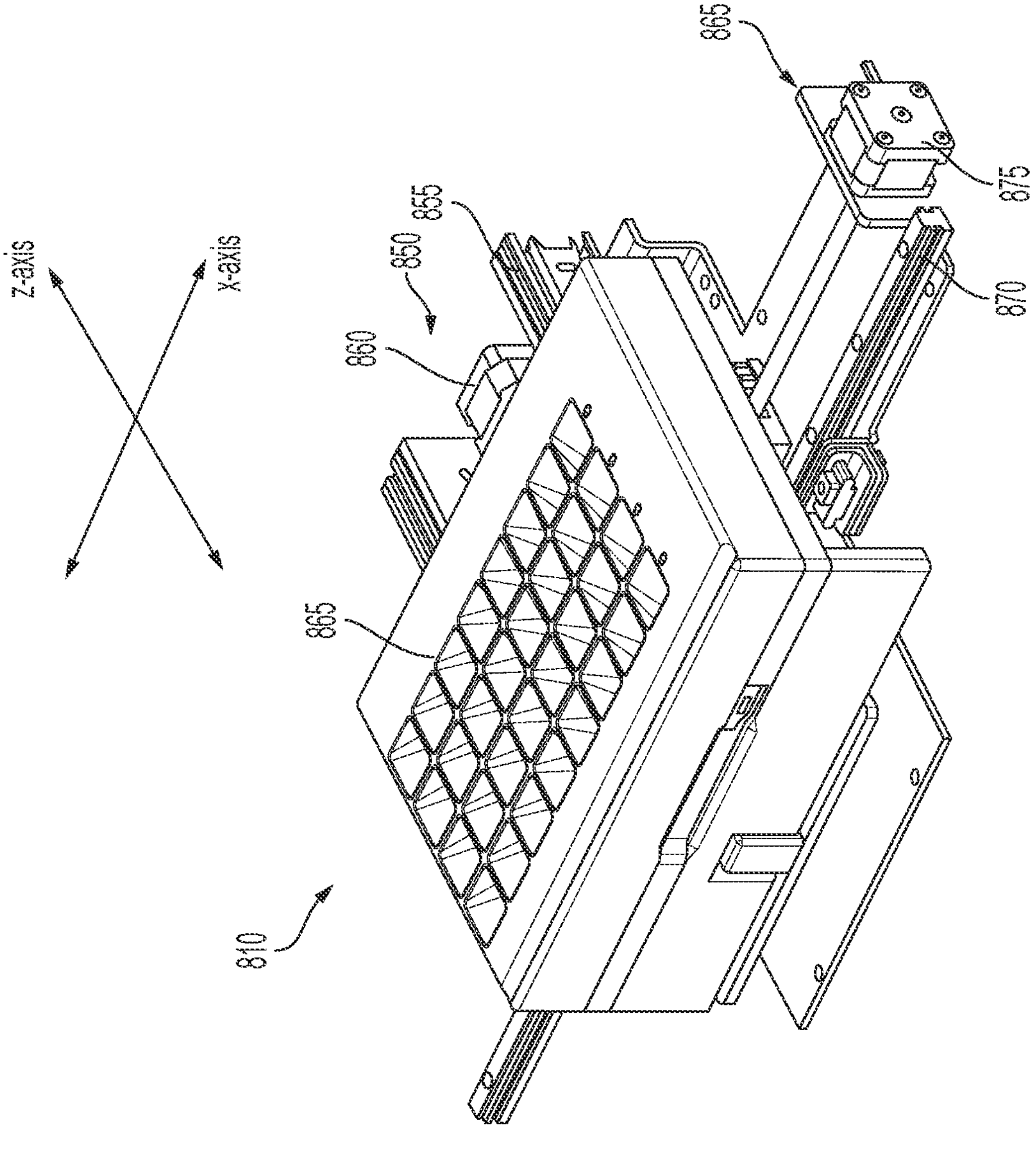
FIGS. 28-30 illustrate the blister card packaging unit of FIG. 27 moved to various positions.
Figure 29:
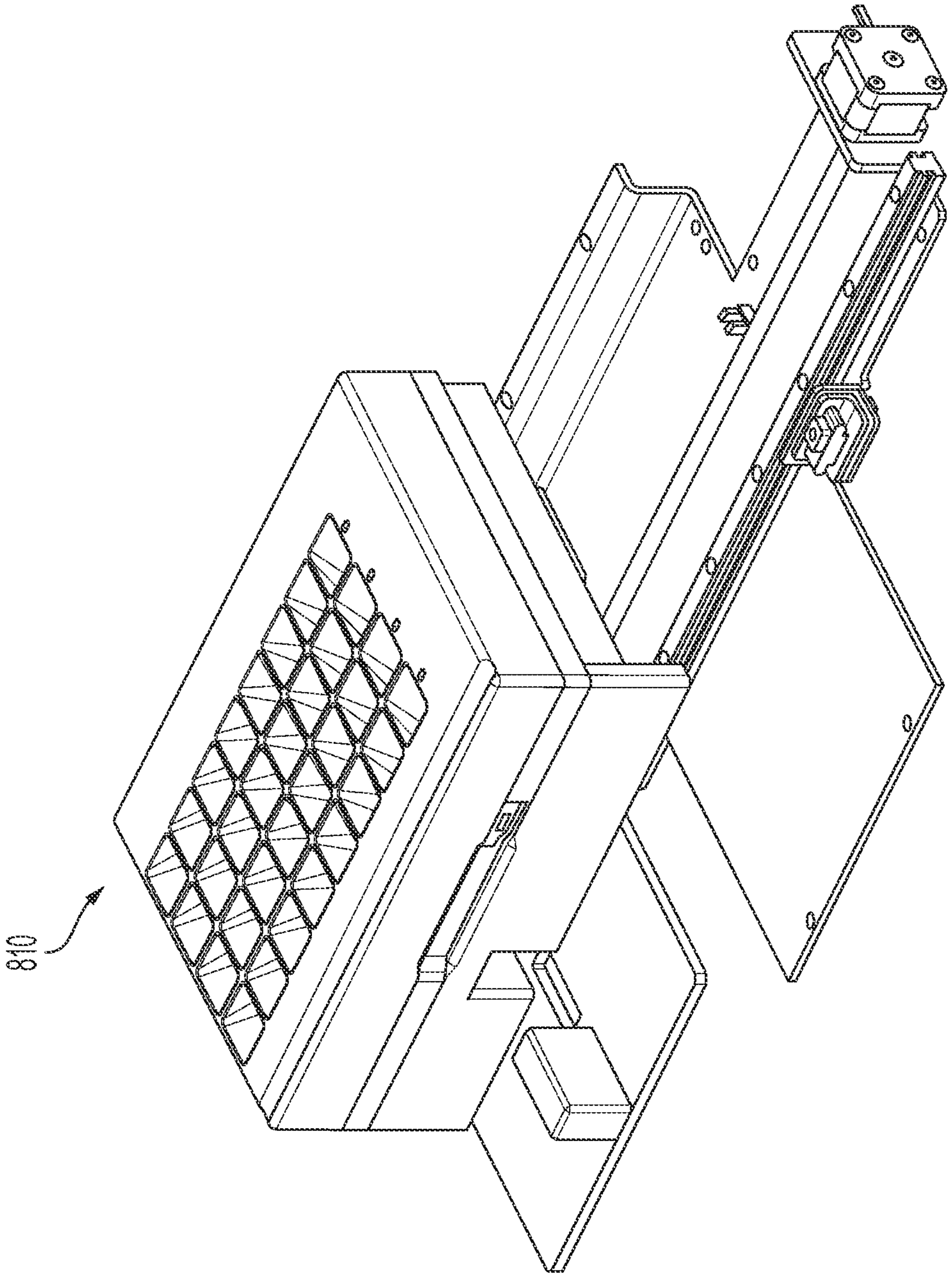
Figure 30:
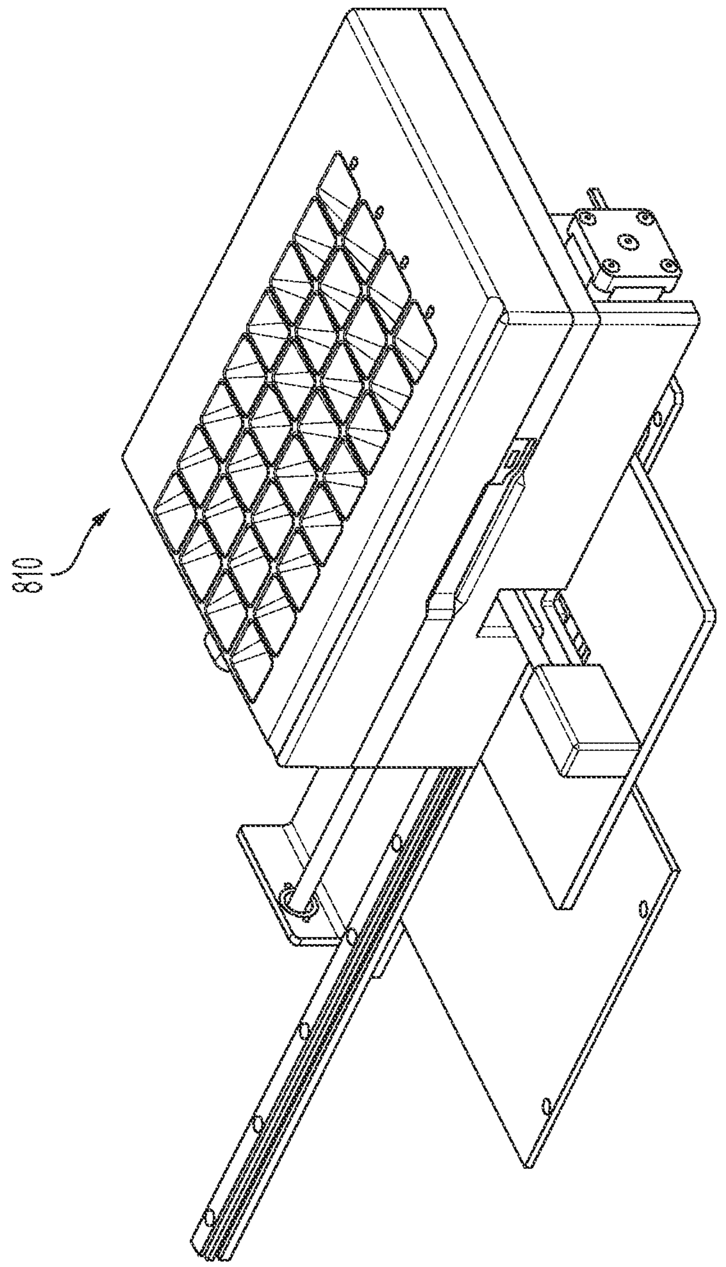

As shown in FIGS. 26 and 27, the blister card packaging unit 810 is movable toward and away from the automatic blister card packager 800, similar to the blister card packaging unit 210 described above. This movement is generally in a forward-backward direction along a first axis. The first axis may also be referred to as a z-axis. In the illustrated embodiment, however, the packaging unit 210 is also movable side-to-side within the automatic blister card packager 800, as shown in FIGS. 28-30. This movement is along a second axis that is perpendicular to the first axis. The second axis may also be referred to as an x-axis. Movement along the first axis is controlled by a first rail system 850 including first rails 855 and a first rail drive 860 (similar to the rail system 505). Movement along the second axis is controlled by a second rail system 865 including second rails 870 and a second rail drive 875. The packaging unit 810 moves forward-backward along the first axis and side-to-side along the second axis to position different openings 865 beneath the manifold 815, as further described below. This is especially useful when filling multiple medications in a single blister compartment 120 as described above.

Figure 31:
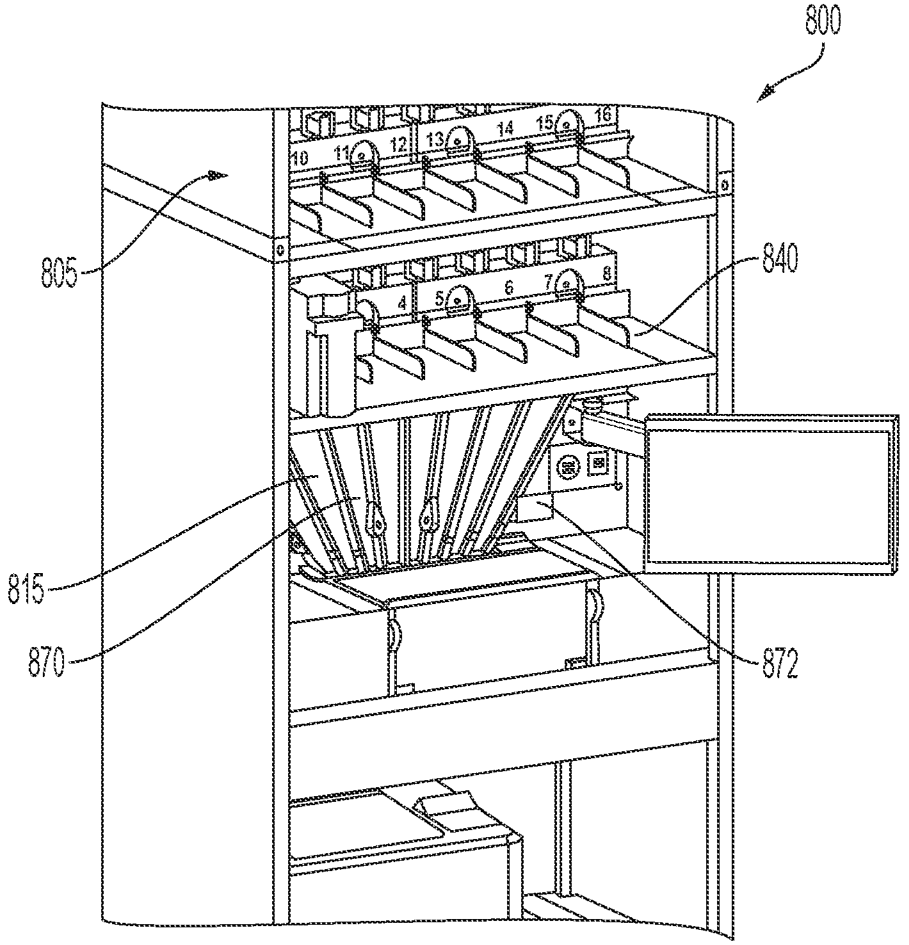
FIG. 31 is an enlarged view of a portion of the automatic blister card packager of FIG. 25 including a manifold in accordance with some embodiments, where the manifold includes separate channels.

FIG. 31 illustrates one example of the manifold 815 for use with the automatic blister card packager 800. The manifold 815 helps direct pharmaceuticals (e.g., pills, vitamins, etc.) from the universal feed cassette 805 to the blister card packaging unit 810. In the illustrated embodiment, the manifold 815 includes eight separate tracks or channels 870. The number of channels 870 correspond to the number of cartridge slots 840 (and thereby cartridges) in each row of the universal feed cassette 805. As such, in some embodiments, the manifold 815 may include fewer or more channels 870. Each channel 870 has a separate outlet that corresponds to one of the openings 865 (FIG. 28) in the packaging unit 810. When pharmaceuticals are delivered from the universal feed cassette 805, the pharmaceuticals travel through the channels 870 of the manifold 815, through the outlets, and into one of the openings 865 in the packaging unit 810. Because the packaging unit 810 can also move side-to-side, the outlets of the manifold 815 do not always necessarily match up with the same openings 865 in the packaging unit 810. In some embodiments, one or more cameras 872 (or sensors) are provided by the channels 870 of the manifold 815 to verify that a pharmaceutical passed through the channels 870. As discussed above, the one or more cameras 872 may be used to detect the presence or absence of an object and/or to detect that a correct number and/or type of pharmaceutical is passing to the channels 870.

Figure 32:
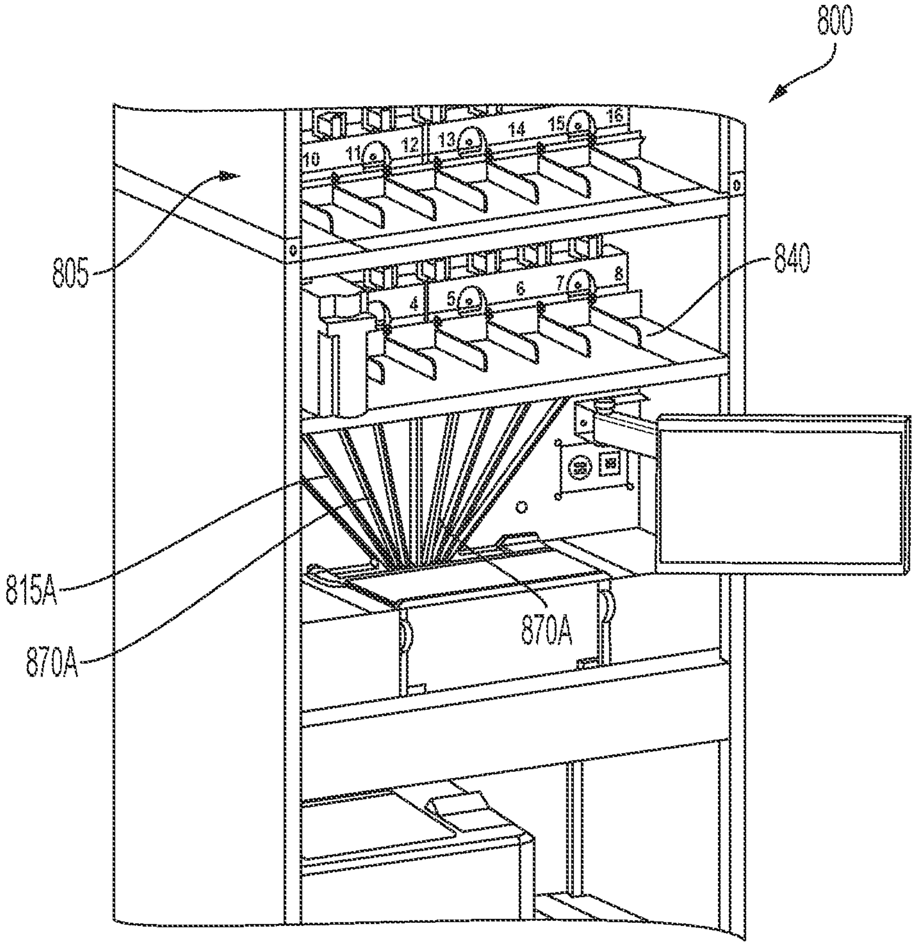
FIG. 32 is an enlarged view of a portion of the automatic blister card packager of FIG. 25 including another manifold in accordance with some embodiments, where the manifold includes a shared channel.

FIG. 32 illustrates another example of a manifold 815A for use with the automatic blister card packager 800. In the illustrated embodiment, the manifold 815A includes two shared tracks or channels 870A that dispense pharmaceuticals through shared outlets to the packing unit 810. For example, four cartridge slots 840 (and thereby cartridges) share one half of the manifold 815A to dispense pharmaceuticals through a first outlet, while four other cartridge slots 840 (and thereby cartridges) share the other half of the manifold 815A to dispense pharmaceuticals through a second outlet. In other embodiments, the manifold 815A may include a single shared track or channel that dispenses pharmaceuticals through a single outlet. The illustrated manifold 815, therefore, can only direct pharmaceuticals to two openings 865 (FIG. 28) of the packaging unit 810 at a time. The packaging unit 810, however, can move side-to-side to align with different openings 865 in a row of openings 865 with the shared outlets of the manifold 815A.

In operation, the different manifolds 815, 815A and side-to-side movement of the blister card packaging unit 810 provide additional benefits for filling a blister card (e.g., the blister card 100 shown in FIG. 1). In particular, the outlets of the manifolds 815, 815A are able to be aligned with any compartment 120 in the blister card 100 to deliver a pill to that compartment 120. As such, pills for a prescription order may be loaded into essentially any cartridge in the universal feed cassette 805. The automatic blister card packager 800 can determine and optimize a travel path for the packaging unit 810 to fill the compartments 120, as needed.

Using the first manifold 815, the cartridges may simultaneously (or relatively simultaneously) release pills to fill a row of compartments 120, the packaging unit 810 may index to the next row of compartments 120 along the first axis (i.e., the z-axis), and the process may repeat until all of the rows of compartments 120 are filled. In some embodiments, the cartridges may release a single pill into each compartment. In other embodiments, the cartridges may release multiple pills into each compartment (e.g., between two and eight pills, depending on the size of the compartment). While one row of cartridges (e.g., the bottom row) is being used to fill the blister card 100, the other row of cartridges (e.g., the top row) may be refilled by a user with the next desired type of pills, or vice versa. Such an arrangement may be particularly useful when the same type of pill is being filled in each compartment 120 of the blister card 100.

Alternatively, only some of the channels 870 may be used to fill the blister card 100. For example, only two of the cartridge slots 840 may include cartridges that contain the desired pills for a particular blister card. In such embodiments, only the channels 870 and outlets associated with those cartridges may be used to direct pills into the blister card 100. After particular compartments 120 in a row are filled, the packaging unit 810 may then move along the second axis (i.e., the x-axis) to fill additional compartments in the row. Once a complete row of compartments 120 is full, the packaging unit 810 may index to the next row of compartments 120 along the first axis (i.e., the z-axis), and the process may repeat. In some embodiments, a complete row of compartments 120 may not be filled before the packaging unit 810 moves on to the next row. Rather, the packaging unit 810 may "zig-zag" along the first and second axes to fill the compartments 120. During this time, the cartridges associated with the other cartridge slots 840 may be refilled, filled with pills for another order, or go unused. This process may be carried out using any number of cartridges and associated channels 870 of the manifold 815, such as one, two, three, four, five, six, or seven.

Using the second manifold 815A, only two of the cartridges (e.g., one of the cartridges associated with each shared channel 870A) may release pills. The pills are then delivered by the shared outlets into the associated compartments 120 of the blister card 100. After particular compartments 120 in a row are filled, the packaging unit 810 may then move along the second axis (i.e., the x-axis) to fill additional compartments 120 in the row. Once a complete row of compartments 120 is full, the packaging unit 810 may index to the next row of compartments 120 along the first axis (i.e., the z-axis), and the process may repeat. Such a process may be used to deliver a single pill to each compartment 120 of the blister card 100. Alternatively, multiple pills may be delivered to each compartment 120 of the blister card 100. For example, more than one cartridge associated with each shared channel 870A may simultaneously (or relatively simultaneously) release a pill into the shared channel 870A to deliver multiple pills to a single compartment 120. Alternatively, each cartridge may release more than one pill into the shared channel 870A. In some embodiments, a complete row of compartments 120 may not be filled before the packaging unit 810 moves on to the next row. Rather, the packaging unit 810 may "zig-zag" along the first and second axes to fill the compartments 120. While the desired cartridges are being used, the other cartridges may be refilled, filled with pills for another order, or go unused.

The cartridges in the cartridge slots 840 of the universal feed cassette 805 may be filled with the same type of pills or may be filled with different types of pills, as needed. As such, the compartments 120 of the blister card 100 may be filled with different pills and/or combinations of pills. For example, a first compartment 120 may be filled one pill of a first type, while a second compartment 120 may be filled one pill of the first type and one pill of a second type. Additionally, another compartment may include two pills of the second type, a pill of a third type, and a pill of a fourth type. As should be readily understood, any combination of number and types of pills per compartment 120 is possible, depending on the size of the compartment 120.

Since the blister card packaging unit 810 is movable side-to-side along the second axis (i.e., the x-axis), the processor of the automatic blister card packager 800 can identify which pills are located within which cartridge and generate an optimal path of travel for the blister card packaging unit 810. The processor can determine which type(s) of pills and how many pills are needed for each compartment, based on the prescription order. The processor can also optimize the path using a cost function based on, for example, how many pills are able to be dropped at a time, and the shortest travel distance to the next set of compartments 120. The processor can then send instructions to the rail drives 860, 875 to move the packaging unit 810. The processor can also send instructions to the universal feed cassette 805 to release pills from the cassettes at particular times. Using either manifold 815, 815A, different pills may be dropped into adjacent or non-adjacent compartments 120 of the blister card 100 at the same time to decrease the fill time of the blister card 100.

Thus, the invention provides, among other things, an automatic blister card packager. Various features and advantages of the invention are set forth in the following claims.

The invention claimed is:

1. An automatic packager for blister cards comprising:

a universal feed cassette including a plurality of cartridges and a plurality of conduits corresponding to the plurality of cartridges, the plurality of cartridges configured to individually dispense medications;

a packaging unit in communication with the universal feed cassette, the packaging unit configured to receive a blister card; and a chute connecting the universal feed cassette to the packaging unit, the chute including a plurality of tracks corresponding to the plurality of conduits, wherein the chute is configured to drop the medications dispensed from the universal feed cassette into the blister card received in the packaging unit, wherein the packaging unit includes a packaging equipment, the packaging equipment including a packaging plate including a blister card receiving portion having a plurality of blister openings, the plurality of blister openings configured to accommodate blister compartments of the blister card.

2. The automatic packager of claim 1, further comprising one or more cameras mounted at or near a junction of the plurality of conduits and the plurality of tracks, the one or more cameras configured to determine whether a correct number, or correct type, or both are being dispensed from the plurality of cartridges.

3. The automatic packager of claim 1, a packaging lid connected to the packaging plate and including medication receiving openings extending from a top side to a bottom side of the packaging lid, wherein medications are directed to the blister compartments through the medication receiving openings.

4. The automatic packager of claim 3, wherein the packaging unit further comprises:

a rail system including a rail base fixed to a frame of the automatic packager, rails provided on the rail base and having fixed rails, first moveable rails, and second moveable rails, the first moveable rails configured to slide along the fixed rails, the second moveable rails configured to slide along the first moveable rails, wherein the packaging equipment is attached to the second moveable rails, and a rail drive configured to move the packaging equipment between a rear of the rail base and a front of the rail base along a length of the rail base.

5. The automatic packager of claim 4, wherein the rail drive further comprises:

a rotating screw; and a magnetic end at an end of the rotating screw; the magnetic end configured to be attached to a corresponding end of the packaging equipment, wherein a magnet is provided on one of the magnetic end and the corresponding end and a magnetic material is provided on the other of the magnetic end and the corresponding end, wherein the rotating screw moves the packaging equipment between a first position and a second position.

6. The automatic packager of claim 5, wherein when in the first position, the packaging equipment is within the automatic packager and inaccessible by a user, and wherein when in the second position, the packaging equipment is accessible by the user.

7. The automatic packager of claim 5, wherein when in the second position, the packaging equipment is configured to be detached from the magnetic end such that the packaging equipment is moved to a third position.

8. The automatic packager of claim 4, wherein the medication receiving openings accommodate medication dispensing openings in the chute.

9. The automatic packager of claim 8, wherein the medication receiving openings include a shape having two straight sides and two curved sides on the bottom side, wherein the medication receiving openings includes a shape that is square or rectangular on the top side, and wherein the medication receiving openings have a larger area on the top side compared to an area on the bottom side.

10. The automatic packager of claim 9, wherein the medication receiving openings further comprise walls extending between the top side and the bottom side, wherein the walls converge between the shape on the top side and the shape on the bottom side to direct the medications from the chute into the blister compartments of the blister card placed in the packaging plate.

11. The automatic packager of claim 8, wherein the rail drive is configured to move the packaging equipment to align the medication receiving openings with the medication dispensing openings of the chute.

12. The automatic packager of claim 8, further comprising:

an electronic processor coupled to the universal feed cassette and the rail drive and configured to move, using the rail drive, the packaging equipment from a second position to a first position, align, using the rail drive, a first row of medication receiving opening with the medication dispensing openings of the chute, instruct the universal feed cassette to dispense the medications, determine that the medications are dispensed, determine whether the blister card in the packaging equipment is filled, align a next row of the medication receiving openings with the medications dispensing openings of the chute when the blister card is not filled, and move, using the rail drive, the packaging equipment from the first position to the second position when the blister card is filled.

13. The automatic packager of claim 1, further comprising:

an intermediate member positioned between the chute and the blister card such the medications are dropped from the chute into the blister card via openings in the intermediate member.

14. The automatic packager of claim 13, wherein the openings are configured to accommodate medication dispensing openings in the chute.

15. The automatic packager of claim 13, wherein the intermediate member is a packaging lid, and wherein the packaging unit includes a packaging equipment, the packaging equipment including wherein the intermediate member is a packaging lid connected to the packaging plate, wherein the opening extend from a top side to a bottom side of the packaging lid.

16. The automatic packager of claim 1, wherein the chute converges from the universal feed cassette to the packaging equipment.

17. The automatic packager of claim 1, further comprising one or more cameras positioned adjacent the plurality of tracks and configured to detect presence or absence of an object passing through the one or more of the plurality of tracks.

18. The automatic packager of claim 1, wherein the packaging unit further comprises:

a rail system configured to support the packaging equipment; and a rail drive configured to move the packaging equipment along a side-to-side axis and a forward-backward axis along a single plane within the automatic packager.

19. The automatic packager of claim 18, wherein the rail system is configured to move the packaging equipment to align different blister compartments beneath the chute.

* * * * *